US011166458B2

(12) United States Patent
Grossman et al.

(10) Patent No.: US 11,166,458 B2
(45) Date of Patent: Nov. 9, 2021

(54) WET WIPES COMPRISING ANTIMICROBIAL COATING COMPOSITIONS

(71) Applicant: ALLIED BIOSCIENCE, INC., Dallas, TX (US)

(72) Inventors: Craig Grossman, Point Roberts, WA (US); Gavri Grossman, Point Roberts, WA (US); Jie Fang, Delta (CA); Misagh Alipour, Surrey (CA)

(73) Assignee: Allied Bioscience, Inc., Plano, TX (US)

( * ) Notice: Subject to any disclaimer, the term of this patent is extended or adjusted under 35 U.S.C. 154(b) by 623 days.

(21) Appl. No.: 15/968,586

(22) Filed: May 1, 2018

(65) Prior Publication Data

US 2018/0243790 A1 Aug. 30, 2018

Related U.S. Application Data

(63) Continuation-in-part of application No. 15/432,352, filed on Feb. 14, 2017, now Pat. No. 10,040,952.
(Continued)

(51) Int. Cl.
*A01N 25/34* (2006.01)
*B05D 7/00* (2006.01)
(Continued)

(52) U.S. Cl.
CPC ............ *A01N 25/34* (2013.01); *A01N 33/12* (2013.01); *A01N 55/00* (2013.01); *A61K 8/0208* (2013.01);
(Continued)

(58) Field of Classification Search
None
See application file for complete search history.

(56) References Cited

U.S. PATENT DOCUMENTS 4,721,511 A 1/1988 Kupits
5,411,585 A 5/1995 Avery et al.
(Continued)

FOREIGN PATENT DOCUMENTS

CN 1538937 10/2004
CN 101827650 9/2010
(Continued)

OTHER PUBLICATIONS

Notice of Preliminary Rejection dated Feb. 25, 2019 in Korean Application No. 10-2013-7038130.
(Continued)

*Primary Examiner* — Michael P. Rodriguez
(74) *Attorney, Agent, or Firm* — Snell & Wilmer L.L.P.

(57) ABSTRACT

A wet wipe is disclosed that provides both contact sanitization of a surface and application of a residual antimicrobial coating on the surface through the same wiping. The wet wipe comprises a substrate such as an absorbent nonwoven fabric and a liquid composition impregnated therein, the liquid composition comprising an organosilane such as the antimicrobial dimethyloctadecyl[3-(trimethoxysilyl)propyl] ammonium chloride, a non-silane quaternary disinfectant, an organic amine, and a solvent. The non-silane quaternary actives comprise a mixture of actives, and the solvent comprises 60 wt. % isopropanol or more.

24 Claims, 12 Drawing Sheets

Wet wipe coatings from PR-103-1

Untouched    Rinsed    Worn 10x

Related U.S. Application Data which is a continuation of application No. 15/432,334, filed on Feb. 14, 2017, now Pat. No. 9,855,584, which is a continuation of application No. 13/448,325, filed on Apr. 16, 2012, now Pat. No. 9,757,769.

(60) Provisional application No. 61/476,233, filed on Apr. 15, 2011, provisional application No. 61/489,630, filed on May 24, 2011.

(51) Int. Cl.
| | |
|---|---|
| *B05D 1/04* | (2006.01) |
| *D06M 23/00* | (2006.01) |
| *D06M 11/46* | (2006.01) |
| *D06M 15/423* | (2006.01) |
| *D06M 13/513* | (2006.01) |
| *A61Q 19/10* | (2006.01) |
| *A61K 8/41* | (2006.01) |
| *A61K 8/898* | (2006.01) |
| *A61K 8/58* | (2006.01) |
| *A61K 8/02* | (2006.01) |
| *A61Q 17/00* | (2006.01) |
| *A01N 33/12* | (2006.01) |
| *A01N 55/00* | (2006.01) |

(52) U.S. Cl.
CPC ............... *A61K 8/41* (2013.01); *A61K 8/585* (2013.01); *A61K 8/898* (2013.01); *A61Q 17/005* (2013.01); *A61Q 19/10* (2013.01); *B05D 1/04* (2013.01); *B05D 7/52* (2013.01); *D06M 11/46* (2013.01); *D06M 13/513* (2013.01); *D06M 15/423* (2013.01); *D06M 23/005* (2013.01); *B05D 2601/24* (2013.01)

(56) References Cited

U.S. PATENT DOCUMENTS

| | | | |
|---|---|---|---|
| 5,569,732 A | 10/1996 | Nohr et al. | |
| 5,954,869 A * | 9/1999 | Elfersy | C07F 7/1804 |
| | | | 106/287.16 |
| 6,037,289 A | 3/2000 | Chopin et al. | |
| 6,180,548 B1 | 1/2001 | Taoda et al. | |
| 6,228,480 B1 | 5/2001 | Kimura et al. | |
| 6,432,191 B2 | 8/2002 | Schutt | |
| 6,436,085 B1 | 8/2002 | Lauer | |
| 7,262,158 B1 | 8/2007 | Lukenbach et al. | |
| 7,541,048 B2 | 6/2009 | DeWitt | |
| 7,763,565 B2 | 7/2010 | Fu et al. | |
| 8,491,922 B2 | 7/2013 | Eddy | |
| 8,968,771 B2 | 3/2015 | Richardson et al. | |
| 2003/0127207 A1 | 7/2003 | Clark et al. | |
| 2004/0023824 A1 | 2/2004 | Zuechner et al. | |
| 2005/0008613 A1 | 1/2005 | Peterson et al. | |
| 2005/0008763 A1 | 1/2005 | Schachter | |
| 2005/0214483 A1 | 9/2005 | Fujieda et al. | |
| 2007/0065475 A1 | 3/2007 | Elfersy | |
| 2007/0167551 A1 | 7/2007 | Goodwin et al. | |
| 2007/0275101 A1 | 11/2007 | Lu | |
| 2008/0305153 A1 | 12/2008 | Wang et al. | |
| 2009/0062111 A1 | 3/2009 | Fu et al. | |
| 2009/0118152 A1 | 5/2009 | Lam et al. | |
| 2009/0209665 A1 | 8/2009 | Fu et al. | |
| 2009/0274914 A1 | 11/2009 | Hoshi et al. | |
| 2009/0298967 A1 | 12/2009 | Taylor et al. | |
| 2010/0028462 A1 | 2/2010 | Bolkan | |
| 2010/0055028 A1 | 3/2010 | Scott et al. | |
| 2010/0075298 A1 | 3/2010 | Creek et al. | |
| 2010/0144518 A1 | 6/2010 | Scott et al. | |
| 2010/0160201 A1* | 6/2010 | Scheuing | C11D 1/83 |
| | | | 510/180 |
| 2010/0267550 A1 | 10/2010 | Fu et al. | |
| 2010/0292185 A1 | 11/2010 | Burns et al. | |
| 2011/0274767 A1 | 11/2011 | Kato et al. | |
| 2012/0291667 A1 | 11/2012 | Geoffrion et al. | |
| 2013/0122074 A1 | 5/2013 | Kerrod et al. | |
| 2017/0088717 A1 | 3/2017 | Grossman | |

FOREIGN PATENT DOCUMENTS

| | | |
|---|---|---|
| CN | 101998979 | 3/2011 |
| EP | 0923988 | 9/2008 |
| JP | 2006326530 | 12/2006 |
| KR | 1019990028236 | 4/1999 |
| KR | 1019990044670 | 6/1999 |
| KR | 100280910 | 2/2001 |
| KR | 1020080093483 | 10/2008 |
| KR | 1020080110268 | 12/2008 |
| KR | 1020090110672 | 10/2009 |
| KR | 1020100080509 | 7/2010 |
| WO | 2009029856 | 3/2009 |
| WO | 2009057046 | 5/2009 |

OTHER PUBLICATIONS

Notice of Preliminary Rejection dated Feb. 25, 2019 in Korean Application No. 10-2013-7038127.
Notice of Preliminary Rejection dated Feb. 25, 2019 in Korean Application No. 10-2013-7038129.
Office Action dated Mar. 15, 2019 in RU Application No. 2017120035.
Final Office Action dated Sep. 18, 2018 in Korean Application No. 10-2013-7030183.
Office Action dated Sep. 21, 2018 in Canadian Application No. 2,833,177.
Office Action dated Oct. 5, 2018 in Mexican Application No. MX/a/2013/012000.
Notice of Allowance dated Nov. 19, 2018 in Korean Application No. 10-2013-7030183.
Non-Filine Office Action dated Nov. 13, 2018 in U.S. Appl. No. 15/373,229.
Office Action dated Dec. 7, 2019 in Indonesia Application No. Wo0201305330.
Notice of Allowance dated Jan. 9, 2019 in Canadian Patent Application No. 2,833,177.
Final office Action dated Mar. 29, 2019 in U.S. Appl. No. 15/373,229.
Notice of Allowance dated May 14, 2019 in U.S. Appl. No. 15/373,229.
Notice of Allowance dated Mar. 29, 2019 in MX Application No. MX/a/2013/01200.
International Search Report and Written Opinion dated Jul. 17, 2012 in Application No. PCT/US2012/033844.
Restriction Requirement dated Apr. 17, 2013 in U.S. Appl. No. 13/708,613.
Restriction Requirement dated Oct. 2, 2013 in U.S. Appl. No. 13/448,325.
International Preliminary Report on Patentability dated Oct. 15, 2013 in Application No. PCT/US2012/033844.
Office Action dated Nov. 19, 2013 in U.S. Appl. No. 13/448,325.
International Search Report and Written Opinion dated Mar. 26, 2014 in Application No. PCT/US2013/073878.
Office Action dated Apr. 8, 2014 in U.S. Appl. No. 13/708,613.
Final Office Action dated Sep. 17, 2014 in U.S. Appl. No. 13/448,325.
Office Action dated Oct. 24, 2014 in U.S. Appl. No. 13/708,613.
Extended European Search Report dated Oct. 28, 2014 in European Application No. 12771919.3.
Office Action dated Dec. 11, 2014 in Chinese Application No. 201280026252.0.
Final Office Action dated Mar. 17, 2015 in U.S. Appl. No. 13/708,613.
Office Action dated Mar. 27, 2015 in U.S. Appl. No. 13/448,325.
International Preliminary Report on Patentability dated Jun. 9, 2015 in Application No. PCT/US2013/073878.
Office Action dated Aug. 4, 2015 in Chinese Application No. 201280026252.0.
Office Action dated Sep. 3, 2015 in U.S. Appl. No. 13/708,613.
Office Action dated Oct. 20, 2015 in U.S. Appl. No. 13/448,325.

(56) References Cited

OTHER PUBLICATIONS

Office Action dated Feb. 6, 2016 in Chinese Application No. 201280026252.0.
Office Action dated Mar. 17, 2016 in Russian Application No. 2013150917.
Final Office Action dated Jun. 1, 2016 in U.S. Appl. No. 13/708,613.
Patent Examination Report No. 1 dated Jun. 3, 2016 in Australian Application No. 2012242454.
Rejection Decision dated Jul. 6, 2016 in Chinese Application No. 201280026252.0.
Office Action dated Jul. 15, 2016 in Russian Application No. 2013150917.
Notice of Allowance dated Oct. 31, 2016 in U.S. Appl. No. 13/708,613.
Office Action dated Jan. 26, 2017 in U.S. Appl. No. 13/448,325.
Notice of Acceptance dated Feb. 8, 2017 in Australian Application No. 2012242454.
Aegis, Mater Label—AEM 5772-5 Antimicrobial—A Silane Quaternary Ammonium Salt, 9 pages, 2006.
Aegis, AEM 5772-5 Antimicrobial—A Silane Quaternary Ammonium Salt, 1 page, 2009.
Agis Environments, "Material Safety Data Sheet," AEM 5772 Antimicrobial (72% Active Concentrate), pp. 1-7, USA, 2004.
Su et al., "Sol-gel preparation and photocatalysis of titanium dioxide," Catalysis Today 96, 2004, pp. 119-126, Elsevier B.V.
Liu et al., "Synthesis and Characterization of Titania Prepared by Using a Photoassisted Sol-Gel Method," Langmuir 2003, pp. 3001-3005.
Decision to Grant dated Feb. 14, 2017 in Russian Application No. 2013150917/05.
Grossman, et al., U.S. Appl. No. 15/432,334, filed Feb. 14, 2017 and entitled "Methods of Preparing Self-Decontaminating Surfaces Using Quaternary Silanes and Titanium Anatase Sol".
Grossman, et al., U.S. Appl. No. 15/432,363, filed Feb. 14, 2017 and entitled "Methods of Preparing Reactive Mixtures of Quaternary Silanes and Titanium(IV)Alkoxides and Polymers Therefrom".
Final Office Action dated May 4, 2017 in U.S. Appl. No. 13/448,325.
Notification of Reexamination dated May 25, 2017 in Chinese Application No. 201280026252.0.
Examination Report dated Jun. 2, 2017 in Australian Application No. 2017202598.
Notice of Acceptance dated Jun. 28, 2017 in Australian Application No. 2017202598.
Notice of Allowance dated Jul. 13, 2017 in U.S. Appl. No. 13/448,325.
EP Examination Report dated Aug. 10, 2017 in EP Application No. 12771919.3.
Office Action dated Jun. 23, 2017 in Mexican Application No. MX/a/2013/012000.
USPTO; Notice of Allowance dated Oct. 5, 2017 in U.S. Appl. No. 15/432,334.
USPTO; Non-Final Office Action dated Oct. 10, 2017 in U.S. Appl. No. 15/432,363.
USPTO; Non-Final Office Action dated Oct. 6, 2017 in U.S. Appl. No. 15/432,352.
Notice of Allowance dated May 10, 2018 in U.S. Appl. No. 15/432,363.
Notice of Allowance dated May 11, 2018 in U.S. Appl. No. 15/432,352.
Examination Report dated Aug. 24, 20148 in Eurpoean Application No. 12771919.3.
First Examination Report dated Jun. 21, 2018 in Indian Application No. 2084/MUMNP/2013.
Office Action dated Jul. 5, 2019 in RU Application No. 2017120035.
Communication Pursuant to Article 94(3) EPC dated Apr. 11, 2018 in European Application 12771919.3.
Notice of Preliminary Rejection dated Mar. 13, 2018 in Korean Application No. 10-2013-7030183 (all references previously disclosed).
2nd Office Action dated Mar. 5, 2018 in Mexican Application No. MX/a/2013/012000.
Office Action dated Feb. 20, 2018 in Canadian Application No. 2,833,177.

\* cited by examiner

FIG. 2A

OPTICAL IMAGE USING TRANSMISSION GEOMETRY WITH 10x OBJECTIVE
IMAGE SIZE: 2.4mm x 1.8 mm

United States Patent US 11,166,458 B2

WET WIPES COMPRISING ANTIMICROBIAL COATING COMPOSITIONS

CROSS-REFERENCE TO RELATED APPLICATIONS

This application is a continuation-in-part of U.S. application Ser. No. 15/432,352, filed Feb. 14, 2017 entitled "COATING COMPOSITIONS COMPRISING POLYMERS HAVING TITANIUM/OXYGEN OR SILICON/OXYGEN BACKBONES." The '352 application is a continuation of U.S. application Ser. No. 15/432,334, filed Feb. 14, 2017 entitled "METHODS OF PREPARING SELF-DECONTAMINATING SURFACES USING QUATERNARY SILANES AND TITANIUM ANATASE SOL" (now U.S. Pat. No. 9,855,584, issued Jan. 2, 2018). The '334 application is a continuation of U.S. application Ser. No. 13/448,325, filed Apr. 16, 2012 entitled "COMPOSITION AND METHOD TO FORM A SELF DECONTAMINATING SURFACE" (now U.S. Pat. No. 9,757,769, issued Sep. 12, 2017). The '325 application claims priority to, and the benefit of, U.S. Provisional Application Ser. No. 61/476,233 entitled "Composition and Method to Form a Self Decontamination Surface," filed Apr. 15, 2011, and U.S. Provisional Application Ser. No. 61/489,630 entitled "Composition and Method to Form a Self Decontaminating Surface," filed May 24, 2011. All of the aforementioned disclosures are incorporated herein by reference in their entireties for all purposes.

FIELD

The disclosure generally relates to chemical compositions and methods used to form antimicrobial coatings on a surface, and in particular, the coating of surfaces by expression of a coating composition from an impregnated substrate.

BACKGROUND

Titanium oxide (e.g., $TiO_2$) is a nontoxic substance widely used in paints, paper, plastics, and toothpaste. It is known in the art that an alkali hydroxide can be added to an aqueous titanium salt solution to produce an amorphous titanium peroxide sol. The titanium peroxide sol can be reacted with an aqueous hydrogen peroxide solution to produce an amorphous titanium peroxide sol, which is then heated to high temperatures to obtain anatase titanium oxide.

Current methods for preparing sheets, coatings, or films comprising titanium oxide require that the titanium oxide particles be sintered at high temperatures (e.g., 200° to 400° C.) in order to firmly support the titanium oxide on a substrate. Using these prior art methods, a titanium oxide compound is deposited onto a substrate, and then baked at approximately 200° to 400° C. to fixedly set the compound on the substrate. The requirement of such high temperatures to cure the titanium oxide limits its utility, such as use of titanium dioxide to create self-decontaminating surfaces by retailers or consumers.

Accordingly, it would be an advance in the art to develop or use a new titanium oxide sheet, coating, or film deposition.

BRIEF DESCRIPTION OF THE DRAWINGS

The disclosure will be better understood from a reading of the following detailed description taken in conjunction with the drawings in which like reference designators are used to designate like elements, and in which:

FIG. 2A illustrates another embodiment of a electrostatic spray apparatus;

DETAILED DESCRIPTION

Figure 1:
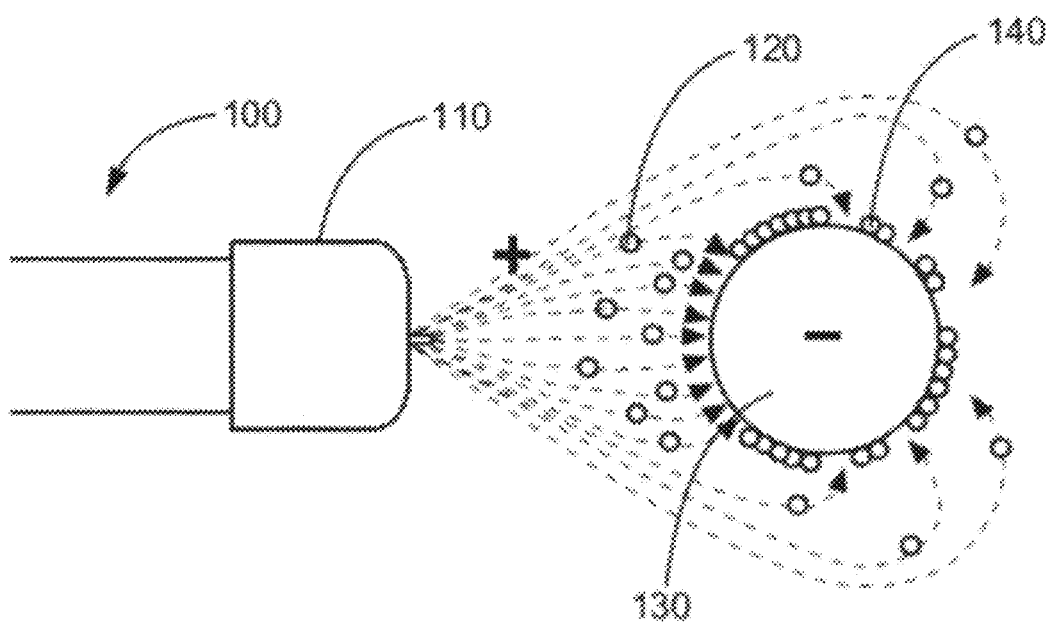
FIG. 1 illustrates one embodiment of a electrostatic spray apparatus.

The disclosure is described in exemplary embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment.

The described features, structures, or characteristics of the disclosure may be combined in any suitable manner in one or more embodiments. In the following description, numerous specific details are recited to provide a thorough understanding of embodiments of the disclosure. One skilled in the relevant art will recognize, however, that the disclosure may be practiced without one or more of the specific details, or with other methods, components, materials, and so forth. In other instances, well-known structures, materials, or operations are not shown or described in detail to avoid obscuring aspects of the disclosure.

Titanium dioxide occurs in nature as well-known minerals rutile, anatase and brookite, and additionally as two high pressure forms, a monoclinic baddeleyite-like form and an orthorhombic α-$PbO_2$-like form, both found recently at the Ries crater in Bavaria. The most common form in is rutile, which is also the most stable form. Anatase and brookite both convert to rutile upon heating. Rutile, anatase and brookite all contain six coordinated titanium.

Titanium dioxide has numerous modifications—in addition to rutile, anatase and brookite there are three metastable forms produced synthetically (monoclinic, tetragonal and orthorombic), and high pressure forms (α-$PbO_2$-like, baddeleyite-like and cotunnite-like):

Oxidation—loss of electrons or an increase in oxidation state by a molecule, atom or ion. Substances that have the ability to oxidize other substances are said to be oxidative or oxidizing and are known as oxidizing agents, oxidants, or oxidizers. Put another way, the oxidant removes electrons from another substance, and is thus itself reduced. And, because it "accepts" electrons, it is also called an electron acceptor.

In chemistry, photocatalysis is the acceleration of a photoreaction in the presence of a catalyst. In catalyzed photolysis, light is absorbed by an adsorbed substrate. In photogenerated catalysis, the photocatalytic activity (PCA) depends on the ability of the catalyst to create electron-hole pairs, which generate free radicals (hydroxyl radicals: •OH) able to undergo secondary reactions. Its comprehension has been made possible ever since the discovery of water electrolysis by means of the titanium dioxide. Commercial application of the process is called Advanced Oxidation Process (AOP). There are several methods of achieving AOP's that can, but do not necessarily, involve $TiO_2$ or even the use of UV light. Generally the defining factor is the production and use of the hydroxyl radical.

When $TiO_2$ is illuminated with light of sufficient energy, electron-hole pairs are excited so that additional electrons go across the band gap to conduction band ("CB"), while holes stay in the valence band ("VB"). The excited electrons may then be used for redox reactions at the surface of $TiO_2$. There are multiple phases of $TiO_2$. For example, Rutile phase can be excited by visible light, but has a fast charge recombination rate; Anatase, on the other hand, has a slow recombination rate, but can only be excited by UV lights. Thus, it is reasonable to produce mixed phase photocatalyst to increase the total efficiency Certain titanium oxide crystalline morphologies exhibit photocatalytic characteristics when exposed to Ultra Violet (UV) light. When exposed to UV light, titanium oxide creates electron-hole pairs which generate free radical (e.g., hydroxyl radicals). The degree of photocatalytic strength varies depending on the type of titanium oxide, for example anatase titanium oxide (particle size of about 5 to 30 nanometers) is a stronger photocatalyst than rutile titanium oxide (particle size of about 0.5 to 1 microns). Therefore, titanium oxide has potential use in sterilization, sanitation, and remediation applications.

In one embodiment of Applicants' composition and method, a titanium oxide coating including an oxidizable pigment is used with an electrostatic sprayer to produce a substantially uniform self-decontaminating coating on a surface.

Referring now to FIGS. 1, 2A, and 2B, in one embodiment, a $TiO_2$ formulation, and/or a $TiO_2$ precursor formulation in the form of a gas, liquid, aerosol, and/or solid is deposited at ambient temperature onto a surface 130. In the illustrated embodiments of FIGS. 1, 2A, and 2B, electrostatic or electrodynamic spray apparatus 100 is used to form a substantially contiguous titanium oxide containing coating 140. Using the electrostatic spray apparatus 100, the atomized particles 120 take on a first electrical charge (shown as positively charged), thereby repelling each other and spreading themselves evenly as they exit a spray nozzle 110. FIG. 2A shows a mixture 220 comprising $TiO_2$ powder in pressurized air being sprayed outwardly from a hand-held spray device 210.

Substrate 130 being coated comprises a second and opposite charge (shown as negatively charged) or grounded. The $TiO_2$ positively charged. $TiO_2$ powder is then attracted to the substrate. The oppositely charged substrate attracts the $TiO_2$ powder particles, even in a "shadowed" rear portion, to give a substantially uniform coating. Use of opposing charges also increases the transfer efficiency and adhesion between the $TiO_2$ particles with the substrate. In some embodiments, the electrostatic spray apparatus may further employ pressure to produce a high-speed air stream that facilitates carrying the atomized particles 120 to the substrate 130.

In certain embodiments, the $TiO_2$ particles are charged to about 30-100 kilovolts by (a) direct charge, (b) tribo charging, or (c) post-atomization charging, for example. In a direct charging, an electrode is immersed in a supply reservoir or conduit including the $TiO_2$. In tribo charging, the inner surface area of the barrel in contact with the $TiO_2$ produces a frictional electrostatic charge as the $TiO_2$ is extruded through the electrostatic spray apparatus. In post-atomization charging, an electrostatic field is applied to the $TiO_2$ downstream of the outlet nozzle. The electrostatic field may be created by electrostatic induction or corona, for example, or by one or more electrodes (electrode ring, mesh or grid).

In certain embodiments, Applicants' composition and method utilize $TiO_2$ in combination with an organosilane comprising a quaternary ammonium moiety. In certain embodiments, that functionalized silane comprises compound 1, wherein R1 and R2 are alkyl, and wherein $X^-$ is selected from the group consisting of chloride, bromide, and iodide. Using this embodiment of Applicants' method, a target surface is coated, partially or entirely, with a mixture comprising Compound 1, and that surface is subsequently coated, partially or entirely, with $TiO_2$.

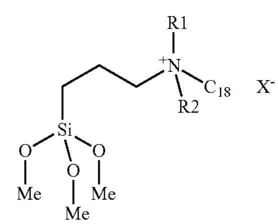

1

The following Examples are presented to further illustrate to persons skilled in the art how to make and use the disclosure. These Examples are not intended as limitations, however, upon the scope of the disclosure.

EXAMPLE I

Two inch square formica[1] coupons were cleaned with soap and water and then isopropyl alcohol. A first group of test coupons was treated using Applicants' method wherein each test coupon was first coated electrostatically using an aqueous mixture comprising 3.6 weight percent organosilane 1. After about fifteen (15) minutes, each of these first test coupons was then electrostatically coated using an aqueous 3 weight percent colloidal suspension of $TiO_2$.

[1] Formica refers to a decorative product composed of several layers of kraft paper impregnated with melamine thermosetting resin and topped with a decorative layer protected by melamine, then compressed and cured with heat to make a hard, durable surface.

A second group of test coupons was coated electrostatically using an aqueous 3 weight percent colloidal suspension of TiO$_2$. A third group of test coupons was coated electrostatically using an aqueous mixture comprising 3.6 weight percent organosilane 1. A control group of test coupons was not coated.

The coated test coupons were then evaluated using Methicillin-resistant *Staphylococcus aureus* ("MRSA") inoculates and in accordance with ASTM E2149-10 Standard Test Method for Determining the Antimicrobial Activity of Immobilized Antimicrobial Agents under Dynamic Contact Conditions. Table 1 recites, for each of the four groups of test coupons, an Initial MRSA Level, a 3 Hour MRSA Level, the percent MRSA remaining after three hours, and a LOG KILL.

TABLE 1

|  | Applicants' Method | TiO$_2$ ONLY | ORGANOSILANE ONLY | CONTROL |
|---|---|---|---|---|
| Initial MRSA Level | 4.80E+07 | 1.90E+07 | 2.60E+07 | 3.00E+07 |
| 3 Hour MRSA Level | 2.50E+05 | 5.00E+05 | 3.20E+05 | 2.80E+06 |
| Percent MRSA Remaining | 0.52 | 2.63 | 1.23 | 9.33 |
| LOG KILL | 2.3 | 1.9 | 1.6 | 1.03 |

The data of Table 1 show that use of only an organosilane coating on the test coupons resulted in about a 2.4 fold increase in the residual MRSA level after three hours compared to use of both an organosilane coating and a TiO$_2$ coating. The data of Table 1 further show that use of only a TiO$_2$ coating on the test coupons resulted in about a 5.1 fold increase in the residual MRSA level after three hours compared to use of both an organosilane coating and a TiO$_2$ coating. In summary, the data of Table 1 demonstrate that treating the test coupons with a first coating of organosilane 1 followed by a coating of TiO$_2$ was much more effective than coating the test coupons with either the organosilane only or with TiO$_2$ only.

EXAMPLE II

A common route of transmission of cold, flu, diarrhea and other common infections is through contact with surfaces contaminated with infectious microorganisms (pathogens). Contamination occurs by settling of droplets from coughs and sneezes onto surfaces, and by touching of surfaces with hands contaminated with pathogens. The pathogens then contaminate the hands of the next person who touches the same surface, and when they bring their hands to their eyes, nose, or mouth infection can result.

Mass transportation systems create an environment in which large numbers of persons on a daily basis share space and interact with surfaces found within system vehicles. A recent study in the United Kingdom demonstrated an increase of respiratory infections (colds and flus) to persons if they had ridden in a bus or streetcar five days previously.

Application of disinfectants on surfaces has been shown to reduce absenteeism and illness in schools. Unfortunately surfaces have to be disinfected on a regular basis to be effective. There are no prior art methods that provide an effective residual property. In marked contrast to prior art methods, Applicants' method creates a surface residual, and therefore, remains effective at reducing pathogen transfer, even if the surface became re-contaminated.

Bacterial contamination of public buses with a California-based public transit authority were characterized in this study and lab analysis was used to determine the efficacy of Applicants' method to minimize exposure to microbial contaminates and odors in public spaces.

Fourteen buses were selected and divided into two groups; one an "experimental" group of seven buses that was treated with the Applicants' method; and one a "control" group of seven buses that received routine transit system treatment. Prior to any treatment, both groups where tested for heterotrophic bacteria in order to establish a baseline profile of each bus. The four-digit code for each bus was recorded.

Samples were taken at five locations in each of the fourteen busses: entry railing, fare box, driver compartment, interior railing, and seat back. Samples were taken at the end of the working day after the bus returned to the transit facility but before they were cleaned by night maintenance workers.

Sites were sampled with a Spongestick (3M, St. Paul, Minn.) containing a neutralizing broth to neutralize any disinfectant that may have been on the sampled area. Approximately 150 sq. cm of the surface was sampled at each selected site in the bus.

All samples were inserted in individual bags that were labeled with a random number code. This procedure was used to prevent workers in the microbiology lab from knowing which samples belonged to which buses, thus establishing a blind study. Once the lab provided the culture results, the codes were used to assign values to the appropriate buses and locations within those buses.

The numbers of heterotrophic bacteria (HPC) were determined on R2A media (Difco, Sparks, Md.) using the spread plate method. Samples were diluted using physiological saline for assay of dilutions. All dilutions were assayed in duplicate. The agar plates were then incubated at room temperature for five days and the resulting colonies of bacteria counted.

A database was developed and all the collected data from the survey and the laboratory analytical data were entered in the database. The data was log transformed and a multiple analyses of variance (ANOVA) were conducted on the data to assess relationships between demographics and characteristics of the surfaces and their use.

Completely randomized designs were used to perform the ANOVA with a rejection region of 5% using the F distribution. Because the distribution of bacteria is not normally distributed (i.e. a bell shaped distribution curve) it is log transformed before analysis.

Log transformation is the conversion of the arithmetic number of bacteria to a $\log_{10}$ (i.e. 100=2, 1,000=3, etc.). The geometric mean (average) is then determined.

Following this procedure used to establish base-line data, the experimental group of 7 buses was treated with the Applicants' method. At the end of thirty days, the same two bus groups (experimental and control) were tested to assess product effectiveness.

Total bacterial numbers or heterotrophic bacteria on hard surfaces are used as a general measure of the sanitization of public surfaces and the effectiveness of cleaning and disinfection of surfaces. The number of bacteria per 150 sq. cm ranged from 80 to 17,200,000 on the surfaces tested. The geometric average number of bacteria in the buses used in this study is shown in Table 2.

Geometric averages are always lower than arithmetic averages as they normalize high and low values. The statistical analysis indicated that there was no statistical difference in the numbers of bacteria in the busses that were selected for treatment and those that were not at the beginning (baseline data) of the study.

TABLE 2

Occurrence of Bacteria in Treated vs. Untreated Buses at Baseline
(Day 0 - before treatment of experimental buses)

| | $Log_{10}$ | | Arithmetic | |
| Parameter | Treated* | Control | Treated | Control |
| --- | --- | --- | --- | --- |
| Number of Samples | 35 | 35 | 35 | 35 |
| Geometric Mean | 2.89 | 3.13 | 776 | 1,349 |
| St. Dev. | 1.13 | 0.75 | 12.3 | 14.5 |

*buses selected for treatment before treatment was applied

After 30 days, data reported in Table 3A demonstrate that there was a significant difference (p=0.005) i.e., a 99.95% probability that there is a difference in the geometric average number of bacteria in the treated and untreated buses. The number of bacteria in the treated buses was significantly less than that found in the untreated buses 30 days after treatment. On average there were 93% fewer bacteria on the surfaces in the treated buses vs. the untreated buses.

TABLE 3A

Bacterial Concentrations in Treated vs. Untreated Buses
After 30 Days

| | $Log_{10}$ | | Arithmetic | |
| Parameter | Treated | Control | Treated | Control |
| --- | --- | --- | --- | --- |
| Number of Samples | 35 | 25* | 35 | 25* |
| Geometric Mean | 3.77 | 4.92 | 5,888 | 83,176 |
| St. Dev. | 1.69 | 1.58 | 48.9 | 38.0 |

*two buses in the control group had been removed from service

The results of Table 3A demonstrate a significant difference between the bacterial load in the [bus] interior of the treated and untreated buses. With the exception of the entry railing, the bacterial burden at all treated sites was reduced as compared to the untreated sites.

The concentration of bacteria at specific sites tested in treated and untreated busses is shown in Table 4 below. The greatest difference between treated and untreated buses in bacteria numbers was in the driver's compartment where there were fewer than 99.8% bacteria in the treated busses. This difference was highly significant (p=0.007).

It appears that the inordinate wear and tear from passenger contact friction on the entrance railings removed Applicants' coating at those places. Table 3B recites the experimental data excluding this site (entrance railing) as an outlier.

After 30 days, with this site excluded, there was a significant difference (p=0.001 i.e. a 99.99% probability that there is a difference) (Table 3B) in the geometric average number of bacteria in the treated and untreated buses. On average there were 97% fewer bacteria on the surfaces in the treated buses vs. the untreated buses.

TABLE 3B

Bacterial Concentrations in Treated vs. Untreated Buses after 30 Days
(Entry Railing Excluded)

| Parameter | $Log_{10}$ Treated | Control | Arithmetic Treated | Control |
| --- | --- | --- | --- | --- |
| Number of Samples | 28 | 20* | 28 | 20* |
| Geometric Mean | 3.42 | 4.91 | 2,630 | 81,283 |
| St. Dev. | 1.48 | 1.52 | 30.2 | 33.1 |

*two buses in the control group had been removed from service

TABLE 4

Bacterial Concentrations at Specific Tested Sites in
Treated and Untreated Buses

| | Treated Bus | | Untreated Bus | | % | |
| Site | Log10 | Arithmetic | Log10 | Arithmetic | reduction | P |
| --- | --- | --- | --- | --- | --- | --- |
| Drivers Compartment | 2.91 | 812.8 | 5.56 | 363,078 | 99.8 | 0.007 |
| Entrance Railing | 5.18 | 151,356 | 4.96 | 91,201 | 0 | 0.75 |
| Seat Backs | 2.84 | 692.8 | 4.49 | 30,903 | 97.8 | 0.071 |
| Interior Railing | 3.36 | 2,291 | 4.25 | 17,783 | 87.1 | 0.222 |
| Fare Box | 4.56 | 36,307 | 5.49 | 309,029 | 88.3 | 0.253 |

This Example II shows that at the beginning of the study there was no statistical difference between levels of bacteria in the buses selected for study. This Example II further shows that the concentration of bacteria was significantly less in the interior of the treated vs. untreated buses after 30 days of use. On average there were 97% fewer bacteria on the interior surfaces of the treated buses in comparison to the same surfaces of the untreated surfaces.

In certain embodiments, Applicants' method utilizes $TiO_2$ in combination with an oxidizable pigment. In certain embodiments, the oxidizable pigment comprises Methylene Blue, Compound 10. The $TiO_2$ is deposited upon the substrate, using a conventional spray means or an electrostatic spray apparatus (collectively the "spray apparatus"). Portions of the substrate coated with the $TiO_2$ particles visually display the color of the oxidizable pigment. For example, portions of the substrate coated with $TiO_2$ particles/Methylene Blue mixture visually appear blue.

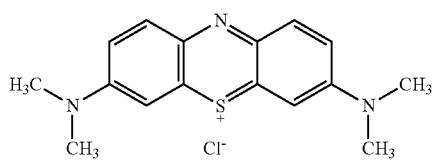

In marked contrast, portions of the substrate not coated with the $TiO_2$ particles do not display the color. A second coating application can be applied to the non-colored portions of the substrate for a more uniform deposition of the $TiO_2$ particles. Exposure of the $TiO_2$ particles to UV light then produces free radicals that oxidize the oxidizable pigment. As a result, a substantially contiguous titanium oxide coating is formed on the substrate, and that coating becomes translucent or white.

Figure 2A:
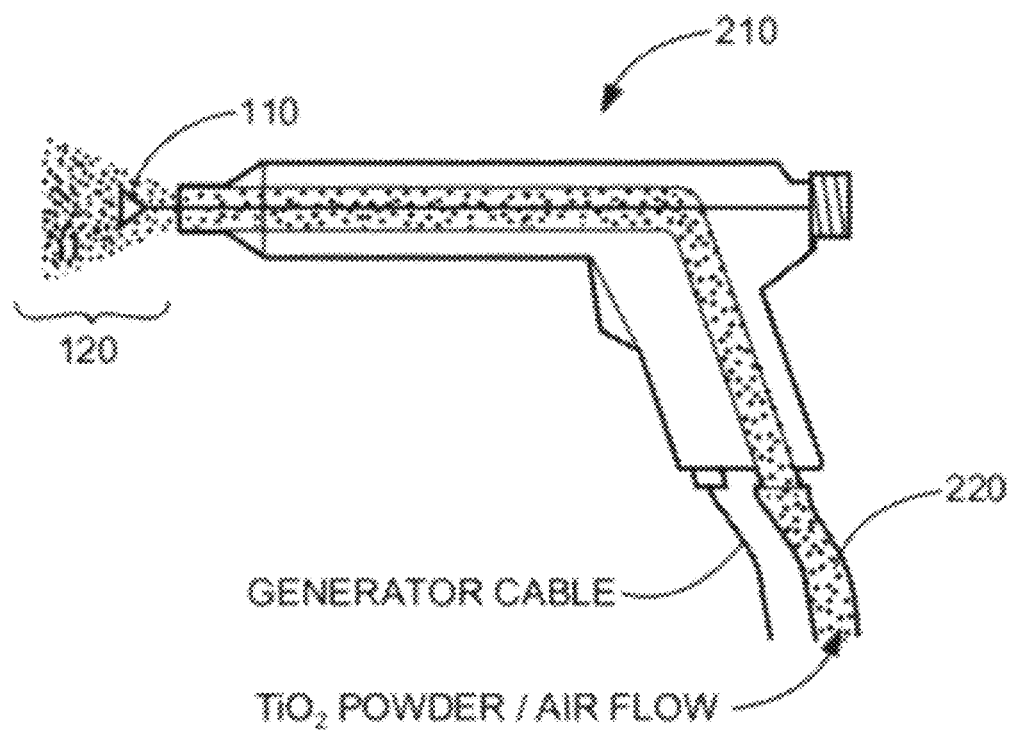
Figure 2B:
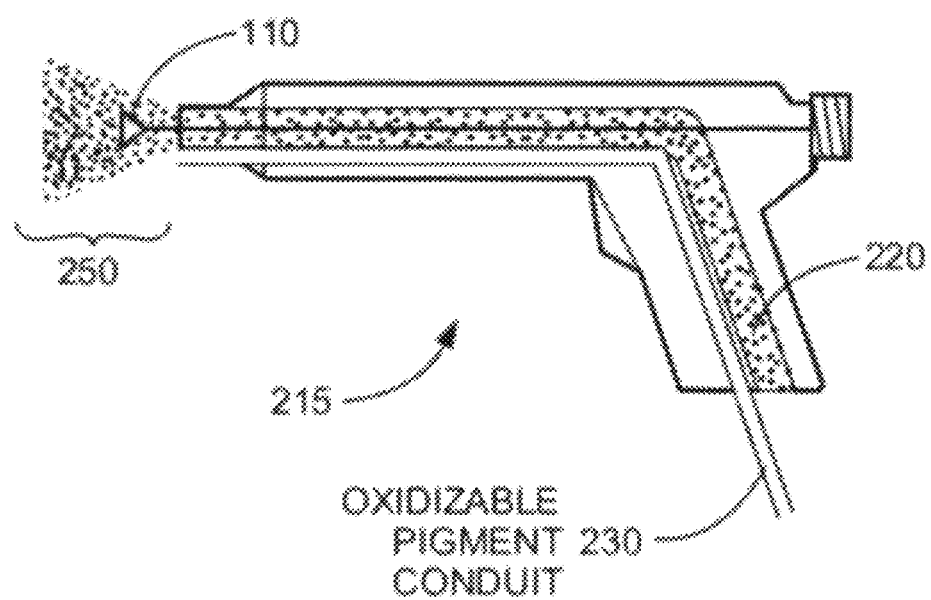
FIG. 2B illustrates the electrostatic spray apparatus of FIG. 2A further comprising a source of oxidizable pigment.

To illustrate, Methylene Blue pigment may be added to the $TiO_2$. In certain embodiments, the Methylene Blue is added directly into the $TiO_2$ powder. In other embodiments, the Methylene Blue is delivered to a nozzle portion of a spray apparatus via an air stream separate from an airstream carrying the $TiO_2$ powder. For example and referring to FIG. 2B, electrostatic hand-held spray device 215 comprises an oxidizable pigment conduit 230. An oxidizable pigment, such as for example Methylene Blue, is discharged from device 215 in combination with $TiO_2$ powder to form a spray 250 comprising charged $TiO_2$ particle and charged Methylene Blue molecules.

The degradation of Methylene Blue after deposition of a $TiO_2$ coating on a substrate is effected by the interaction with the electron-hole pair (e-CB-h+VB). Houas A, Lachheb H, Ksibi M, Elaloui E, Guillard C, and Herrman J-M, Photocatalytic degradation pathway of Methylene Blue in water. Appl Catal B 31, 145-57 (2001) proposed the mechanism of Scheme I.

SCHEME I

1. $TiO_2$ + photon ⟶ e-CB + h + VB
2. $O_2$ (ads) + e-CB ⟶ $O_2$•—
3. ($H_2O$ ⟷ H+ + OH—) (ads) + h + VB ⟶ H+ + •OH
4. $O_2$•— + H+ ⟶ $HO_2$•
5. $2HO_2$• ⟶ $H_2O_2$ + $O_2$
6. $H_2O_2$ + e- ⟶ •OH + OH—
7. Methylene Blue(ads) + •OH ⟶ degradation products In step (2) of Scheme I, $O_2$(ads) comes from ambient $O_2$ present in the system and was adsorbed onto the surface of the $TiO_2$. Methylene Blue has a cationic configuration thus it should be favorably adsorbed to the negative sites of the h-$TiO_2$ surface, e.g., Ti—O(-) and subsequently attacked by the very active •OH moiety, leading to the destruction of the Methylene Blue molecule.

Various embodiments of Applicants' method and composition provide a titanium alkoxide starting material $(RO)_4Ti$ photocatalyst surface coating precursor. For example, in certain embodiments Applicants' method forms a liquid coating composition using titanium tetraisopropoxide 2, and casts that coating composition solution onto a surface to form a coating comprising a linear polymeric structure 3 on the surface.

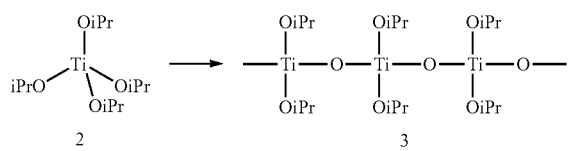

In other embodiments, Applicants' method forms a liquid coating composition using titanium tetraisopropoxide 2, and casts that coating composition solution onto a surface to form a coating comprising a cross-linked structure 4 on the surface.

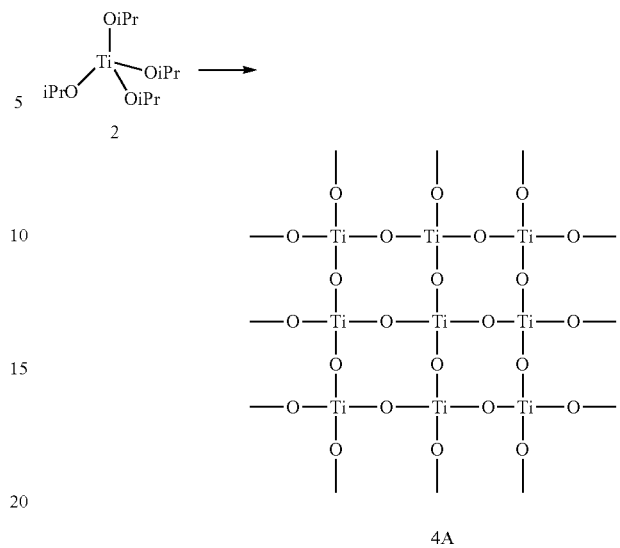

4A

The following Example III is presented to further illustrate to persons skilled in the art how to make and use the disclosure. This example is not intended as a limitation, however, upon the scope of the disclosure.

EXAMPLE III 9.0 grams of tartaric acid were dissolved in 0.120 liters of water in an Erlenmeyer flask to give a 0.5 molar solution. This solution was stirred overnight at room temperature. The following day, the tartaric acid solution was filtered through filter paper (Whatman #1), then subsequently through a 0.2 micron PRFW filter to remove particulates. 25 mL of filtered 0.5 M tartaric acid (0.01249 moles of tartaric acid) was poured into a round bottom flask and chilled on ice with stirring. 3.69 grams of titanium (IV) isopropoxide was added slowly first with a 1 mL addition. 1 mL aliquots of titanium (IV) isopropoxide were added until all of it was added to the tartaric acid solution.

Upon addition of the titanium (IV) isopropoxide the ice bath was removed. The solution remained a solution for approximately 10 minutes after which it became a clear gel and became progressively opaque (white). The gel was stirred at RT overnight. The gelatinous material was mixed with water, or isopropanol and water, and then cast onto a glass surface to form a coating thereon. In certain embodiments, Applicants' coating of this Example II comprises a tartaric acid/titanium isopropoxide repeat unit 11A, wherein (r) is between 1 and about 10. In certain embodiments, Applicants' coating of this Example III comprises a tartaric acid/titanium isopropoxide adduct 11B.

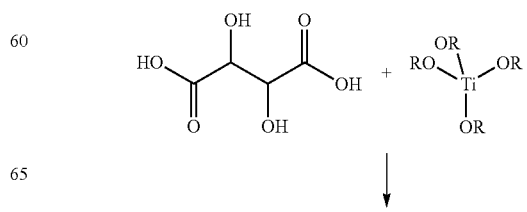

-continued

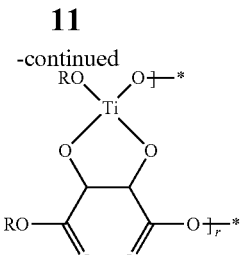

11A

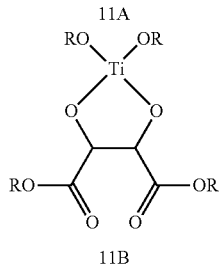

11B

In other embodiments, Applicants' coating composition comprises one or more hydroxyl acids other than tartaric acid in combination with $TiO_2$. In certain embodiments, these one or more hydroxyl acids include one or more alpha hydroxyl acids including glycolic acid, lactic acid, citric acid, and/or mandelic acid. In certain embodiments, these one or more hydroxyl acids include one or more beta hydroxyl acids including salicylic acid and/or beta-hydroxypropionic acid.

Figure 3:
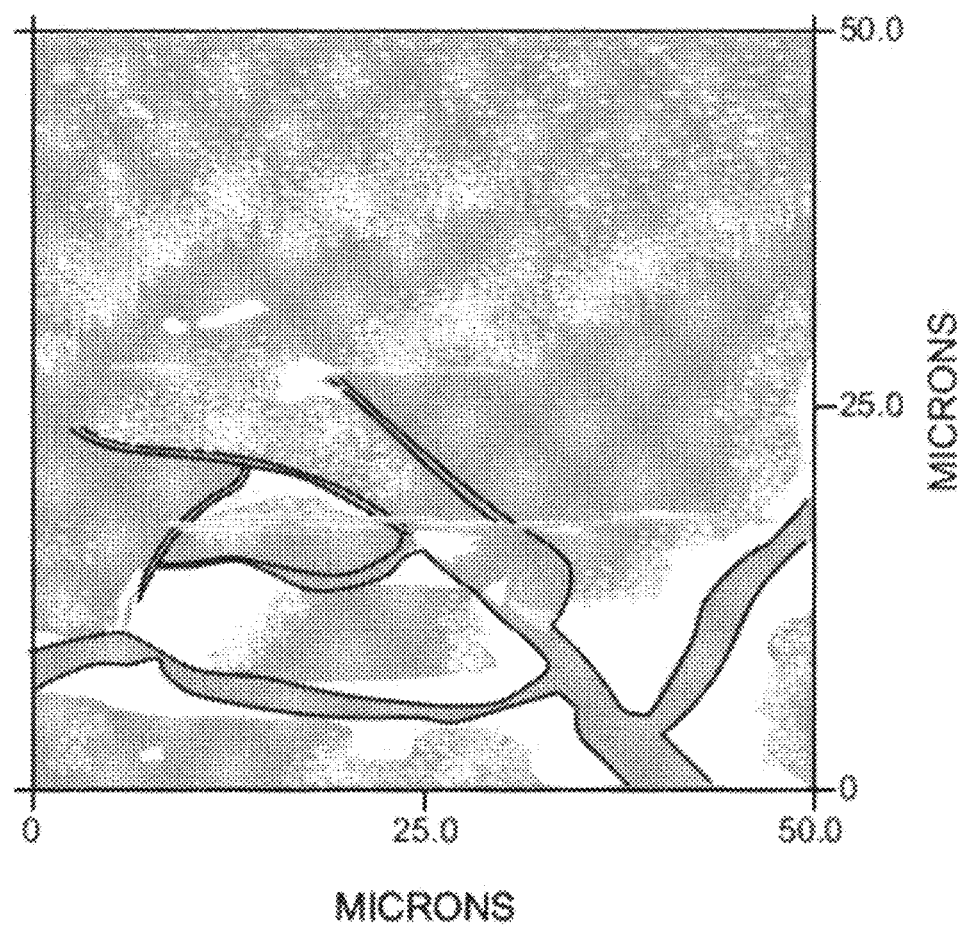
FIG. 3 is an Atomic Force Microscope image at 50 microns showing a coating on a glass surface, where that coating was formed using Applicants' composition and method.
Figure 4:
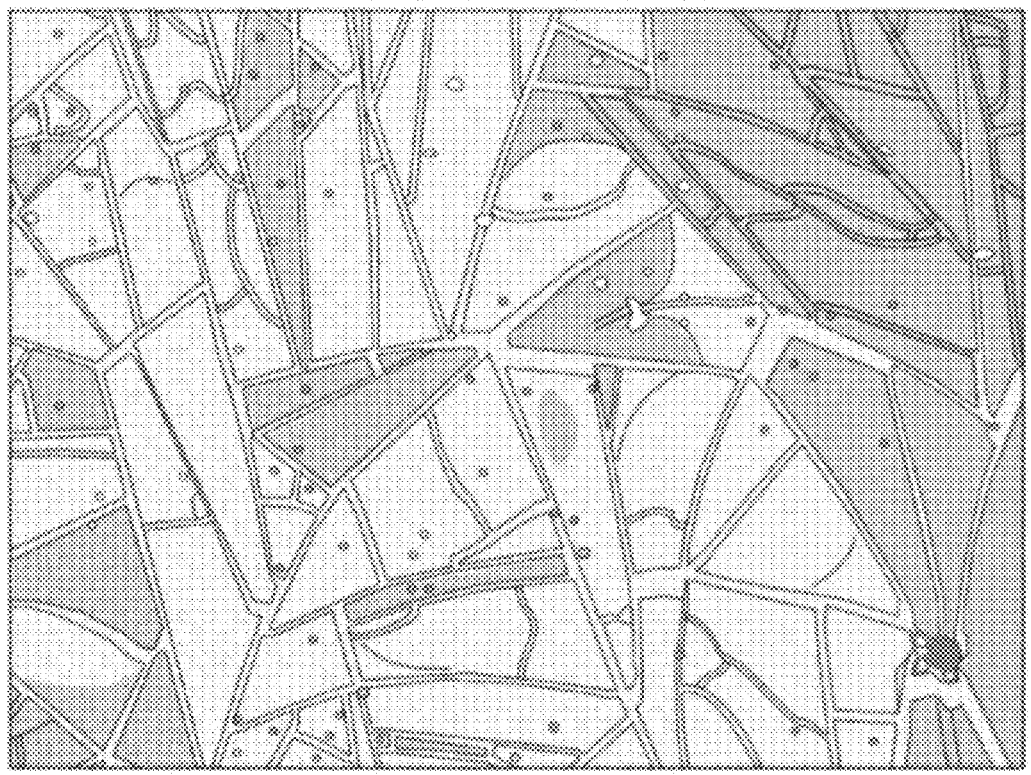
FIG. 4 is an optical image using transmission geometry with 10× objective showing a coating on a glass surface, where that coating was formed using Applicants' composition and method.

FIGS. 3 and 4 show images of the coating formed on the glass surface. FIG. 3 is an Atomic Force Microscope image at 50 microns. FIG. 4 is an optical image using transmission geometry with 10× objective.

In certain embodiments, Applicants utilize silane alkoxide 5, wherein silane alkoxide 5 comprises a quaternary ammonium salt. In certain embodiments, R5 is selected from the group alkyl, and oxyalkyl. In certain embodiments, R6 is selected from the group consisting of alkyl, alkenyl, phenyl, and benzyl. In certain embodiments, R7 is selected from the group consisting of alkyl, alkenyl, phenyl, and benzyl. In certain embodiments, R8 is selected from the group consisting of alkyl, alkenyl, phenyl, and benzyl. In certain embodiments, R8 comprises C18 alkyl.

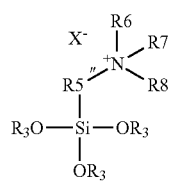

5

In certain embodiments, an embodiment of Compound 5 is prepared from choline 12 and silyl ester 13 to form an ammonium silyl ester 14, wherein (p) is between 1 and about 5, and wherein R is selected from the group consisting of methyl and ethyl.

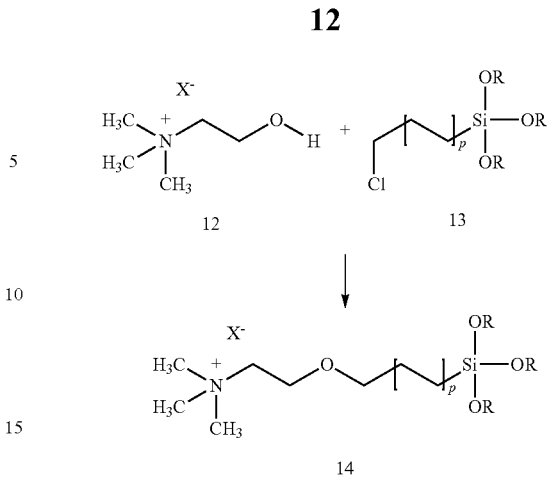

In certain embodiments, Applicants' method prepares a polymeric material 6 and/or polymeric material 8 using titanium alkoxide monomer 2 and silane alkoxide monomer 5.

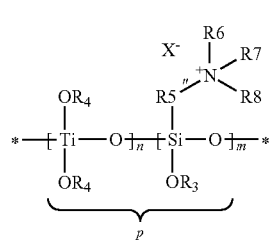

6

In certain embodiments, Applicants utilize Titanium alkoxide 7 to prepare a self-decontaminating coating.

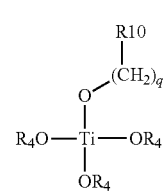

7

In certain embodiments, q is between 1 and about 10. In certain embodiments, R10 comprises a chromophore that upon exposure of electromagnetic radiation having a first frequency emits electromagnetic radiation having a second frequency, wherein the second frequency differs from the first frequency. In certain embodiments, the first frequency is within the ultraviolet spectrum and the second frequency is within the visible spectrum. Those of ordinary skill in the art will appreciate that a typical human eye will respond to wavelengths from about 390 to 750 nm.

Figure 5:
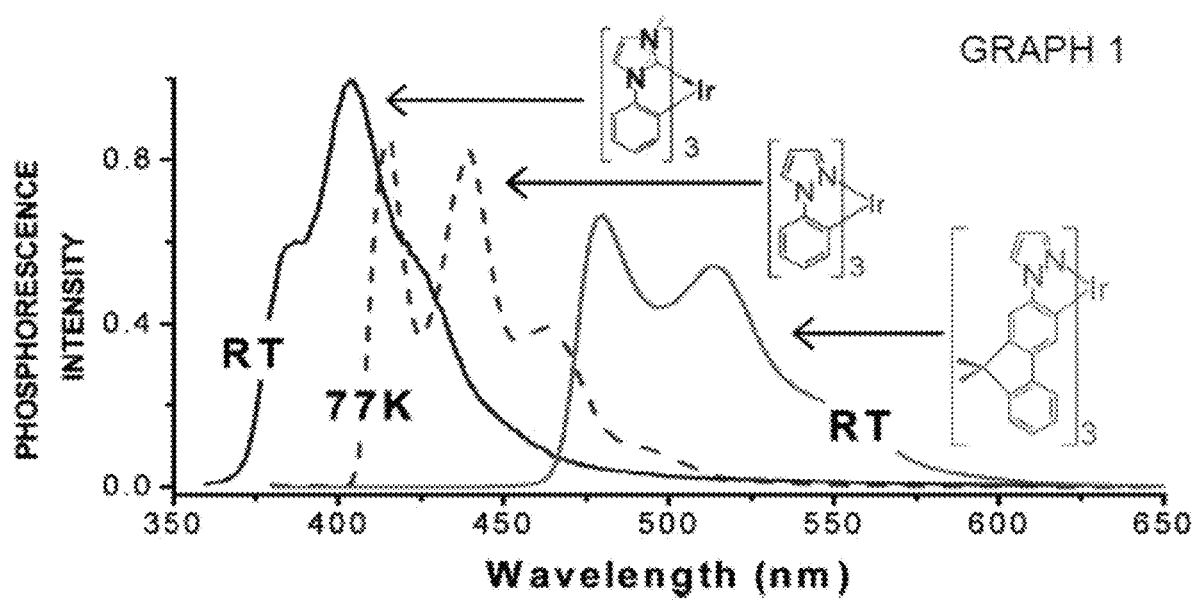
FIG. 5 is a graph showing the emission spectra for three different triscyclometalated iridium(III) materials.

In certain embodiments, R10 comprises a triscyclometalated iridium(III) material that, upon UV irradiation, emits light in the visible spectrum. Graph 1 in FIG. 5 shows the emission spectra for three different triscyclometalated iridium(III) materials.

In certain embodiments, Applicants' method prepares a polymeric material 8 using titanium alkoxide monomer 2 and silane alkoxide monomer 7. In certain embodiments, Applicants polymeric material 8 is prepared from polymeric material 6.

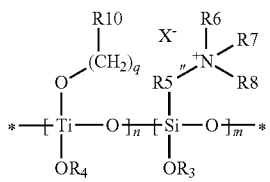

In certain embodiments, Applicants prepare a polymeric material 6 and/or polymeric material 8 wherein n=0, p=1, and m=1 to about 500. In certain embodiments, Applicants prepare a polymeric material 6 and/or polymeric material 8 wherein m=0, p=1, and n is 1 to about 500.

In certain embodiments, Applicants' method disposes a first coating on a surface wherein said first coating comprises polymeric material 6 and/or polymeric material 8 wherein n=0, p=1, and m=1 to about 500. In certain embodiments, the first coating is applied using the electrostatic spray assembly of FIG. 2A and/or FIG. 2B. Applicants' method then disposes a second coating on the same surface over the first coating, wherein the second coating comprises polymeric material 6 and/or polymeric material 8 wherein m=0, p=1, and n=1 to about 500. In certain embodiments, the second coating is applied using the electrostatic spray assembly of FIG. 2A and/or FIG. 2B.

In certain embodiments, Applicants prepare a polymeric material 6 and/or polymeric material 8 wherein n is between about 5 and 500, and wherein m is 1, and wherein p is 1. In certain embodiments, Applicants prepare a polymeric material 6 and/or polymeric material 8 wherein n is between about 5 and 500, and wherein m is 2, and wherein p is 1, such that polymeric material 6 and/or polymeric material 8 comprises a titanium/oxygen backbone with silyl ester end groups. In certain embodiments, Applicants prepare a polymeric material 6 and/or polymeric material 8 wherein n is between about 5 and 500, and wherein m is 2, and wherein p is 1, such that polymeric material 6 and/or polymeric material 8 comprises a titanium/oxygen backbone with silyl ester end groups, wherein that polymeric material comprises a substantially linear structure. In certain embodiments, Applicants prepare a polymeric material 6 and/or polymeric material 8 wherein n is between about 5 and 500, and wherein m is 2, and wherein p is 1, such that polymeric material 6 and/or polymeric material 8 comprises a titanium/oxygen backbone with silyl ester end groups, wherein that polymeric material comprises a cross-linked structure.

In certain embodiments, Applicants prepare a polymeric material 6 and/or polymeric material 8 wherein m is between about 5 and 500, and wherein n is 1 and wherein p is 1. in certain embodiments, Applicants prepare a polymeric material 6 and/or polymeric material 8 wherein m is between about 5 and 500, and wherein n is 2, and wherein p is 1, such that polymeric material 6 and/or polymeric material 8 comprises a silicone/oxygen backbone with titanyl ester end groups.

In certain embodiments, Applicants prepare a polymeric material 6 and/or polymeric material 8 wherein m is between about 5 and 500, and wherein n is 2, and wherein p is 1, such that polymeric material 6 and/or polymeric material 8 comprises a silicone/oxygen backbone with titanyl ester end groups, wherein that polymeric material comprises a substantially linear structure. In certain embodiments, Applicants prepare a polymeric material 6 and/or polymeric material 8 wherein m is between about 5 and 500, and wherein n is 2, and wherein p is 1, such that polymeric material 6 and/or polymeric material 8 comprises a silicone/oxygen backbone with titanyl ester end groups, wherein that polymeric material comprises a cross-linked structure.

Applicants' method includes forming a coating composition comprising a polymeric material 6 and/or polymeric material 8 wherein m is between about 5 and 500, and wherein n is 2, and wherein p is 1, and casting that coating composition onto a substrate to form a self-decontaminating surface on that substrate. Applicants method includes forming a coating composition comprising a polymeric material 6 and/or polymeric material 8 wherein n is between about 5 and 500, and wherein m is 2, and wherein p is 1, and casting that coating composition onto a substrate to form a self-decontaminating surface on that substrate.

In certain embodiments, Applicants prepare a polymeric material 6 and/or polymeric material 8 wherein n is between about 1 and 10, and wherein m is between about 1 and 10, and wherein p is between about 1 and 10. In certain embodiments, Applicants prepare a polymeric material 6 and/or polymeric material 8 wherein n is between about 1 and 10, and wherein m is between about 1 and 10, and wherein p is between about 1 and 10, such that the polymeric material comprises titanyl ester end groups, wherein that polymeric material comprises a substantially linear structure. In certain embodiments, Applicants prepare a polymeric material 6 and/or polymeric material 8 wherein n is between about 1 and 10, and wherein m is between about 1 and 10, and wherein p is between about 1 and 10, such that the polymeric material comprises titanyl ester end groups, wherein that polymeric material comprises a cross-linked structure.

In certain embodiments, Applicants prepare a polymeric material 6 and/or polymeric material 8 wherein n is between about 1 and 10, and wherein m is between about 1 and 10, and wherein p is between about 1 and 10, such that the polymeric material comprises silyl ester end groups, wherein that polymeric material comprises a substantially linear structure.

In certain embodiments, Applicants prepare a polymeric material 6 and/or polymeric material 8 wherein n is between about 1 and 10, and wherein m is between about 1 and 10, and wherein p is between about 1 and 10, such that the polymeric material comprises silyl ester end groups, wherein that polymeric material comprises a cross-linked structure.

Applicants method includes forming a coating composition comprising a polymeric material 6 and/or polymeric material 8 wherein n is between about 1 and 10, and wherein m is between about 1 and 10, and wherein p is between about 1 and 10, such that the polymeric material comprises silyl ester end groups, and casting that coating composition onto a substrate to form a self-decontaminating surface on that substrate. Applicants method includes forming a coating composition comprising a polymeric material 6 and/or polymeric material 8 wherein n is between about 1 and 10, and wherein m is between about 1 and 10, and wherein p is between about 1 and 10, such that the polymeric material comprises titanyl ester end groups, and casting that coating composition onto a substrate to form a self-decontaminating surface on that substrate.

Wet Wipe Embodiments

In certain embodiments, Applicants' coating composition is embodied in a flexible, planar member to form a composite disinfecting wipe. Applicants' composite disinfecting wipe is capable of cleaning and removing residues from soiled surfaces while simultaneously destroying undesirable microorganisms, e.g. bacteria, mold, viruses, prions and the like that colonize on common surfaces with which people come into contact, such as doorknobs, countertops, toilet seats, floors, beds, walls, and the like.

In other aspects, various coating compositions disclosed herein may be impregnated into a substrate, and the resulting wet wipe used to deliver coating compositions onto a surface. Use of a wet wipe to deliver a surface coating composition offers an attractive alternative to spray coating. Use of a wet wipe to deliver a liquid coating is in many ways more convenient and less expensive than spray coating. For example, instead of electrostatically spraying a coating composition onto a surface, the antimicrobial coating compositions may be delivered to a surface through a wet wipe capable of expressing the liquid composition from the substrate onto a surface. Further, safety issues associated with inhalation of fine aerosol droplets are eliminated, such as seen when sprayers are incorrectly selected or adjusted and produce too fine a mist of irritants.

In other examples, a wet wipe article in accordance to the present disclosure functions both by killing germs present on a surface by wiping the article over the germs, and by leaving behind a film of liquid composition that subsequently dries into a coating that exhibits extended antimicrobial benefit. In other words, the liquid expressed from a wet wipe herein is effective both when wet and when dry. Thus, in some embodiments, a wet wipe article herein functions as a contact disinfecting wipe and as a delivery vehicle providing a residual sanitizing coating on that surface. This dual action ensures a surface is cleaned and disinfected, and thus in better condition for a residual antimicrobial coating. In many examples, the residual liquid film on a surface after the surface is wiped is thin enough that drying is rapid at ambient conditions.

As disclosed in more detail below, two different types of compositions may be delivered from a wet wipe herein, namely an organosilane composition and a titanium composition. In certain examples, a canister with two separate compartments may be employed wherein one roll or stack of substrate sheets saturated with an organosilane composition occupies one compartment, while a second roll or stack of substrate sheets saturated with a titanium composition occupies the second compartment. In this way, the single integral dispenser provides both compositions as wet wipes, such that each composition can be applied separately and sequentially to a surface. A user may pull one wet wipe out from one compartment and wipe down a surface, and then pull one wet wipe out from the other compartment and wipe down the same surface. This two-step wiping process with two different wet wipes functions as an alternative to the two-step spraying procedure for treating a surface, as discussed and exemplified in EXAMPLE I herein above. In other aspects, an organosilane and a titanium species may be combined in a single mixture, such as exemplified above with organosilane (5) and titanium (IV) isopropoxide (2), impregnated into a wipe substrate. In this way, the wipe would contain various silane-titanium polymers, such as (6) and (8) as discussed above.

In various embodiments, a wet wipe comprises: (a) a substrate; and (2) a liquid composition impregnated therein. The substrate may comprise a flexible absorbent material such as a woven or nonwoven fabric or a porous plastic sheet. As mentioned, the liquid composition may comprise an organosilane or a titanium species. The wet wipe is an article of manufacture comprising both a substrate portion and a liquid portion. A liquid composition is absorbed into the substrate to produce the wet wipe article. The liquid composition may be described as per any chemical formulation, such as by weight percentages of the active and inert ingredients, totaling to 100%. Once the liquid composition is absorbed into the substrate, the option exists to describe weight percentages based on the total weight of the article of manufacture. These weight percentages that take into account the weight of the substrate in the wet wipe article are sometimes useful for regulatory reasons, and may be required for an EPA registration.

In various aspects of the present disclosure, the term "substrate" refers to sheet-like absorbent material having sufficient absorptive capacity to hold a liquid impregnated within its void structure, i.e., within the interstices between fibers or inside fine capillary channels in porous plastic structures. Flexible thin substrates are familiar to one skilled in the art of disinfectant wipes, and to many lay individuals who use disinfecting wipes or other wetted cloths or wipers around the home and institutions. No theories are proposed as to how liquid is held within a substrate, as it is commonly known that a liquid will wick into a porous or fibrous structure and remain in the structure until it is squeezed back out.

Herein, a substrate is typically quite thin, such as on the order of less than 100 mil thickness (<0.10 inches). In various examples, a substrate is less than about 50 mils thick, less than about 20 mils thick, or less than about 10 mils thick. Thickness may also be reflected in the basis weight of a substrate, which is a measure of the density of the fabric and necessarily factors in the weight of the substrate. Basis weight is expressed in ounces/square yard, or "osy" units of measurement. For use herein, a substrate will typically have a basis weight of between about 0.5 osy and about 40 osy. In some examples, a substrate for use herein has a basis weight of less than about 10 psy, and in some instances, less than about 5 osy. Substrates for use herein may be of any color. For example, a nonwoven may be naturally white to light grey because of the plastics used and the processing to obtain the sheets, but any substrate, regardless if natural or synthetic, may be colored, such as for marketing reasons. Natural substrates may be dyed like clothing, and plastic substrates may have added dyes or pigments to the polymeric starting materials such that the plastic products are colored.

For use herein, a substrate may be of any length and any width, and there may be different dimensions between substrate prior to processing and substrate in the form of a wet wipe ready for sale. For example, huge bolts of substrate may be obtained, which are then rewound into smaller length rolls and cut to particular widths, such as from about 5 to about 10 inches, such as to fit inside a plastic dispensing container, like a box or canister. In some instances, rolls of substrate may be perforated at any time during processing, such that individual wet wipe sheets can be obtained from a roll by tearing or snapping across each successive perforation. Typically a roll of substrate will measure about 5 to about 10 inches in width, and of sufficient length on the roll to provide for at least about 50 wipers, each about 5-10 inches in length, or any number that suffices for the target market. In some examples, an individual wiper, such as one removed from a roll across a perforation, will measure about 5-10 inches in both width and about 5-10 inches in length. In some examples, a substrate roll is stood up vertically within a cylindrically shaped canister so that each wipe can be pulled out through the top of the canister, from the outside or the inside of the roll. Although relative, the "width" of a roll standing vertically inside a cylindrical canister may be viewed as the "height," and often the wicking rate of the substrate is considered in production wherein a dry substrate roll is first dropped into a dry canister and then a liquid is added to the canister that is intended to be absorbed into the dry substrate roll. In some instances, the lower portions of the roll (closest to the bottom of the canister) may have absorbed more liquid than the upper portions of the roll, simply because of gravity and the inability for the roll to wick the liquid all the way to the very top. Nonetheless, this shortcoming is often rectified in the dispensing process where a wet wipe is pulled through a constriction in the lid of the canister, effectively squeegeeing off excess liquid back into the canister and evening out the liquid across the substrate sheet. Or in some instances, an excess of liquid is added to the canister such that the entire roll is saturated to the top and liquid remains loose in the bottom of the canister.

In other embodiments, wet wipes are provided in a fan-folded arrangement inside a plastic box. The interlocking fan-folded arrangement allows for successive individual wet wipes to be removed from a slot in the box, with the next one pulled up by pulling out a first wipe. This is the same arrangement as a box of dry tissues and a number of "baby wipe" products in retail.

For use herein, a substrate may have any absorptive capacity needed for a particular application of antimicrobial coating composition. Substrate absorptivity is sometimes expressed in grams/square area of substrate, e.g., 2.6 grams/ 4" by 4" sheet. Other substrates may have absorptive capacity reported as porosity, e.g., a volume per square area of substrate. Substrates for use herein have an absorptive capacity of from about 0.05 to about 0.5 grams/sq. inch. An exemplary substrate is reported to have an absorptive capacity of 2.6 grams/4" by 4" sheet, which equates to about 0.16 grams/sq. inch. Achieving the maximum absorptive capacity of a substrate with a liquid, or at least close to the maximum, also depends on the surface tension of the liquid wicked into the interstices of the substrate, and in some instances, ingredients in the liquid, such as surfactants or solvents, reduce the surface tension of the liquid to below that of water, enabling absorptivity of the liquid into the substrate. Further, a liquid having lower surface tension will wick faster into a substrate, and these wicking rates are sometimes of interest in manufacturing wet wipes.

Substrates for use herein may comprise natural materials (e.g. paper, cotton), synthetic materials (e.g., polyolefin like polyethylene or polypropylene, or polyester), or combinations of the two (e.g. pulp wetlaid or airlaid onto a plastic webbing). In various embodiments, a substrate comprises a woven or a nonwoven fabric. In other embodiments, a substrate comprises a thin sheet of porous plastic, such as obtained by sintering plastic particles in a mold or during rolling or extrusion. In the case of thin flexible porous plastic sheets, the substrate is not considered fabric at all.

Woven fabric substrates may be synthetic or natural, examples including but not limited to woven polyester (synthetic) and woven cotton (natural) or blends thereof. Woven substrates may resemble the materials commonly seen in clothing, (polyester, cotton, cotton/poly, spandex, and the like). Nonwovens are more prevalent in the wipes industry. These materials comprise randomly or directionally laid fibers. Typical nonwovens that find use as substrates herein include various meltblown, spunbond, airlaid, wetlaid and needlepunch fabric substrates, such as available from the Kimberly-Clark Company, Atlanta, Ga. or Deitsch Plastic, West Haven, Conn. Of particular importance are polyethylene, polypropylene, polyester, acrylic, rayon, 4DG polyester, and blends of these plastic materials in the form of meltblown, spunbond, airlaid, wetlaid and needlepunch nonwoven fabric. Also of importance are the unidirectional nonwoven fabrics, such as those comprising polyethylene filaments laid parallel in a resin matrix. Natural substrates are available from the Fort James Corporation, acquired by Georgia Pacific LLC and now a subsidiary of Koch Industries. The substrates available from Fort James include pulp-based substrates. Various substrates usable for the wet wipes herein are disclosed in U.S. Pat. No. 6,841,527, assigned to the Clorox Co., and in U.S. Pat. No. 8,563,017, assigned to the Kimberly-Clark.

As used herein, the term "impregnated" is a relative term meant to describe that a dry substrate is wet with any amount of a liquid composition such that the liquid is absorbed into the substrate. Absorptive capacity is mentioned herein above, and an impregnated substrate may be at any level of saturation relative to its absorptive capacity. In other words, an impregnated substrate may be only partially wetted. In other examples, an impregnated substrate may be completely saturated, i.e., treated with sufficient liquid composition such that the absorptive capacity has been reached. As mentioned, impregnated substrates for use as wet wipe articles may be wet beyond saturation, such that the wet wipe is sitting in excess liquid while in a dispensing container. In some instances, it is better to over-saturate rather than under-saturate a substrate with a disinfecting solution, particularly if a minimum amount of liquid is required by an EPA disinfectant registration. In these instances, excess solution can always be expressed back into the dispensing container when a single wet wipe is pulled from the container for use, such as through a dispensing closure that squeegees the wet wipe as it is pulled out through the closure. Further, over-saturation is a way to compensate for evaporation during storage of wet wipe products.

In various embodiments, a wet wipe article of manufacture comprises (1) a substrate; and (2) a liquid composition impregnated therein, wherein the liquid composition comprises: (a) at least one organosilane; (b) at least one non-silane quaternary disinfectant; and (d) a solvent. In various examples, the solvent comprises both isopropanol and water. In various embodiments, the liquid composition further comprises an organic amine. In certain examples, the liquid composition further comprises at least one stabilizer, such as 3-chloropropyltrimethoxysilane and/or methyltriethoxysilane.

In various embodiments, an organosilane may be present in the liquid composition at from about 0.1 to about 5 wt. % total organosilane, based on the total weight of the composition. The silanes may include both antimicrobial silanes and silanes functioning as surface bonding agents and/or solution stabilizers.

In various embodiments, a non-silane quaternary disinfectant may be present at from about 0.001 to about 1 wt. % total active non-silane quaternary, based on the total weight of the composition. In certain examples, the total amount of a mixture of non-silane quaternary species is from about 0.3 to about 0.5 wt. %, based on the total weight of the liquid composition impregnated into the substrate.

In various embodiments, an organic amine may be present at from about 0.001 to about 3 wt. %, based on the total weight of the composition.

In various embodiments, a solvent is present at "q.s.", that is, in "quantity sufficient" to mathematically bring the formulation up to 100 wt. % total. In various examples, solvent may be present at from about 85.0 to about 99.9 wt. %, based on the total weight of the composition. The solvent may consist entirely of water, or may consist entirely of a non-water solvent such as an alkanol. That is, the liquid composition may comprise an aqueous liquid composition.

In other examples, the solvent may comprise any mixture of water with one or more non-water solvents. In some instances, the amount of non-water solvent, such as isopropanol (IPA), may exceed the amount of water. For example, a liquid composition for use in a wet wipe may comprise from about 40 to about 60 wt. % of IPA or more, based on the total weight of the liquid composition.

In various examples, the at least one organosilane comprises dimethyloctadecyl[3-(trimethoxysilyl)propyl] ammonium chloride, (referred to herein as "DMOD"). This silane is expressly included in the genus Compound 1 above, wherein R1 and R2 are each methyl, and X— is chloride. As discussed, this organosilane is antimicrobial and surfaces coated with this material exhibit residual antimicrobial efficacy as demonstrated herein. In other examples, the organosilane comprises any other species encompassed by the genus Compound 1, or mixtures thereof, of any hydrolysis product therefrom. Although compositions are formulated with DMOD, it is recognized that this substance could likely hydrolyze to dimethyloctadecyl[3-(trihydroxysilyl)propyl] ammonium chloride. For simplicity, it is the amount of DMOD used to initially formulate a liquid composition in a wet wipe that is referred to herein in various formulation tables, regardless that the material may hydrolyze in the aqueous conditions.

In various aspects, the at least one organosilane comprises 3-chloropropyltrimethoxysilane (referred to herein as CPTMS), or its hydrolysis product wherein the three methoxyl substituents on the silicon atom are replaced by hydroxyl groups. In some examples, the at least one organosilane comprises a mixture of DMOD and CPTMS, and or partial or complete hydrolysis products therefrom.

In various aspects, the at least one organosilane comprises methyltriethoxysilane, referred to herein as MTES, or its partial or complete hydrolysis product(s).

In various examples, the organosilane comprises any combination of DMOD, CPTMS and MTES. In certain examples, the organosilane comprises a mixture of DMOD and MTES, without CPTMS.

In various embodiments, a non-silane quaternary disinfectant is also included in the liquid composition portion of the wet wipe. The term "non-silane" is used to distinguish the disinfectant from DMOD, also a quaternary ammonium species and an antimicrobial. The non-silane quaternary disinfectants used herein comprise any quaternary ammonium chloride species known to exhibit antimicrobial efficacy. These quaternary ammonium antimicrobials (also known as "quats") are supplied by Lonza, Stepan, and Pilot (having acquired the quats from Mason Chemical) and others, under various brand names, such as Bardac® and Barquat® from Lonza, BTC® and Stepanquat® from Stepan, and Mason® from Pilot. It should be noted that most of these quaternary compounds are mixtures of active materials in order to achieve broad spectrum antimicrobial efficacy, and most of these further comprise mixtures of alkyl chain lengths. Further, these commercial materials may be sourced at 50% or 80% active levels, and thus are used at an amount sufficient to provide from about 0.001 to about 1 wt. % of total non-silane quaternary actives, based on the total weight of the liquid in the wet wipe. In various examples herein, more than one commercially available non-silane quaternary disinfectant may be used in the wet wipe composition, such as to achieve even broader spectrum contact disinfection and/or to obtain a more efficacious residual antimicrobial coating after drying of the composition on the surface. It should also be noted that some of these branded products are chemically identical.

Of use herein are the following non-limiting examples of non-silane quaternary disinfectants: BTC®-1210 (mixture of n-alkyldimethylbenzyl ammonium chloride and didecyldimethyl ammonium chloride); BTC®-1010 (didecyldimethyl ammonium chloride); BTC®-2125M (mixture of n-alkyldimethylbenzyl ammonium chloride and n-alkyl dimethylethylbenzyl ammonium chloride); Stepanquat® 2125M (mixture of n-alkyldimethylbenzyl ammonium chloride and n-alkyl dimethylethylbenzyl ammonium chloride); BTC®-885 (mixture of n-alkyldimethylbenzyl ammonium chloride and dialkyldimethyl ammonium chloride); BTC®-8358 (n-alkyldimethylbenzyl ammonium chloride); Bardac® 205M (mixture of alkyldimethylbenzyl and dialkyldimethyl ammonium chloride); Barquat® MB-80 (alkyldimethylbenzyl ammonium chloride); Mason® CS 125 (50% active alkyldimethylbenzyl ammonium chloride, with a distribution of chain lengths C12 67%, C14 25%, C16 7%, and C18 1%); Mason® CS-15M and 24M (mixture of dialkyldimethyl ammonium chlorides and alkyldimethylbenzyl ammonium chloride); and Mason® CS-425 (50% active alkyldimethylbenzyl ammonium chloride having a chain length distribution of C12 40%, C14 50%, C16 10%, and C16 10%). This list is not meant to be limiting in any sense, but is instead intended to show the breadth of non-silane quaternary disinfectants available for use in a wet wipe. A wet wipe according to the present disclosure may comprise any of these or other quaternary disinfectants in any combination.

In certain examples, a composition for impregnating into a wipe substrate to form a disinfecting wet wipe comprises from about 0.001 to about 1 wt. % active BTC®-1210, which is a mixture of n-alkyldimethylbenzyl ammonium chloride having an n-alkyl distribution of 50% C14, 40% C12, and 10% C16, and didecyldimethyl ammonium chloride; BTC®-1010, which is solely didecyldimethyl ammonium chloride; and/or BTC®-2125M, which is a mixture of n-alkyldimethyl ammonium chloride having an n-alkyl distribution of 60% C14, 30% C16, 5% C12 and 5% C18, and n-alkyldimethylethylbenzyl ammonium chloride having an n-alkyl distribution of 68% C12 and 32% C14, and wherein the ethylbenzyl substituent may comprise a mixture of regioisomers having the ethyl group at various positions on the phenyl ring. In various examples, the total amount of non-silane quaternary, whether comprising a single quaternary disinfectant or a mixture of quaternaries, is from about 0.001 to about 1 wt. %, based on the total weight of the liquid composition. Thus, for example, a mixture of quaternary disinfectants may be used in a liquid composition for a wet wipe such that there is a total active level of quaternary of about 0.3 to about 0.5 wt. %, based on the total weight of the liquid composition. In various examples herein, several different species of actives are provided by mixing three of the commercially available products, each one of which is a mixture of actives.

In various embodiments, a liquid composition in a wet wipe further comprises an organic amine. This amine may be any primary, secondary or tertiary amine, having any combination of linear or branched alkyl or aryl substituents on N, including nitrogen heterocyclic compounds. Examples include, but are not limited to, triethylamine, dimethyloctadecylamine, diethanolamine, triethanolamine, morpholine, pyrrolidine, and the like. In various embodiments, the amine comprises triethanolamine. In various example, an organic amine is present at from about 0.001 to about 3 wt. %, based on the total weight of the liquid composition absorbed into the substrate. In certain examples, the organic amine is present from about 0.02 to about 0.06 wt. % based on the total weight of the liquid composition.

In certain aspects, the solvent in the wet wipe liquid composition consists essentially of water. However, in other examples the solvent may comprise a mixture of water along with an alcohol or glycol, such as, ethanol, n-butanol, t-butanol, n-propanol, i-propanol, propylene glycol, and the like. In various examples, the wet wipe liquid component comprises a mixture of water and isopropanol. In certain examples, the liquid composition used to impregnate a substrate may comprise from about 40 to about 80 wt. % isopropanol, based on the total weight of the liquid composition. In other examples, the liquid composition may comprise from about 40 wt. % to about 60 wt. % isopropanol. In some examples, a liquid composition impregnated in a substrate comprises about 60 wt. % isopropanol.

WET WIPE EXAMPLES

General Procedures (a) Wet Wipes Comprising Nonwoven Substrate and Antimicrobial Liquid Impregnated Therein In these examples, Avant Gauze Sponge NON21444 was used as the nonwoven substrate for each exemplary disinfectant wet wipe. In spite of the name "sponge," this material comprises thin flexible rayon/polyester nonwoven fabric. Each sheet of this material was 4-ply and measured 4"×4". Each 4"×4" piece was folded in half twice, to create a 2"×2" pad. Each substrate, while dry, weighed from about 1.05 grams to about 1.15 grams. Thus, this substrate has a basis weight of approximately 3 osy.

The dry substrate sheet after folding was placed inside a dry, sealable plastic bag. 6.4 grams (approx. 7.5 mL of solution, depending on formulation) of a liquid composition selected from TABLES 5, 8, 11, 13, or 15 was added to the bag and the bag was sealed. The liquid composition was allowed to fully absorb into the substrate, and the wet wipe resulting therefrom was left sealed in the bag until use. The substrate comprised about 14.7 wt. % and the liquid composition comprised about 85.3 wt. %, based on the total weight of the wet wipe article. Thus, for the wet wipes herein, the substrate comprises about 12-15 wt. % of the finished article, and the liquid comprises about 85-88 wt. % of the article, based on the total weight of the wet wipe. The liquid compositions used to wet the substrate in the wet wipe examples that follow are set forth in TABLES 5, 8, 11, 13 and 15.

(b) Test Carriers

As indicated for some of the examples, the test carriers were 3"×1" borosilicate glass microscope slides. These microscope slides are typically about 1 mm thick. The transparency of the test slides made it possible to judge the transparency of the various coatings and to visualize the evenness of coatings after a staining protocol. DMOD coatings were typically entirely transparent. Slides were checked for chips, scratches and cracks, and the defective slides rejected. Slides were cleaned by rinsing in tap water, soaking for 1 hour in reagent alcohol, rinsing three times in deionized water, then drained and dried vertically in a microscope slide box.

As indicated for other examples, the test carriers comprised glass petri dishes. In those examples, the inside of the bottom portion of the dish was used in the same way as the microscope slides.

(c) Coating Clean Test Slides with Antimicrobial Coatings Using a Wet Wipe

The general procedure used to coat a clean microscope slide was to first unseal and remove the wet wipe from its plastic pouch. The wipe was opened and folded around a gloved finger, and the finger was used to wipe the wet wipe up and down the length of the slide three times, for a total of six passes, in the course of about 5 seconds. The coated slides were dried overnight in ambient conditions prior to any abrasion, rinsing, or antimicrobial efficacy testing.

(d) General Procedure for Preparing *S. epidermidis* Bacterial Cultures

1. A culture of *S. epidermidis* ATCC 12228 in 20 ml TSB was prepared with vigorous shaking and incubated 18 to 24 h.

2. The bacteria were allowed to sit for 15 min and, without disturbing debris at the bottom, 0.5 mL of a working solution was removed (0.025 ml BSA, 0.035 ml yeast extract, 0.1 ml mucin and 0.34 ml bacteria). In various examples, this procedure was scaled up to provide 4 mL working solution (4.4 ml TSB, 0.2 ml FBS, 0.4 ml bacteria).

(e) General Procedure for Inoculating a Clean Petri Dish Carrier to Test Contact Disinfection 5×10 μL spots of the bacteria culture were placed in the bottom of each petri dish carrier. The carriers were then transferred to an incubator (37° C.) with lids ajar for 1 hour to dry.

(f) General Procedure for Inoculating a Slide Previously Coated with an Antimicrobial Coating—Testing Residual Sanitizing Efficacy 1. 10 μL of the culture solution was inoculated on the right side of a previously coated microscope slide and the inoculum spread over one third of the slide surface using a bent tip. The inoculum was not allowed to touch the edges of the slide. Time duration was started with spreading of the bacteria.

2. The inoculated slides were carefully transferred to the incubator (37° C.), and slides were removed at selected times for quantification of bacteria remaining.

3. Following the prescribed duration, 20 ml D/E broth was added to 50 ml conical tubes and the inoculated end of the slides were immersed in the solution.

4. Each tube was vortexed for 2 min, and 10-fold serial dilutions were prepared therefrom and plated on TSA plates. CFU counts were made between 30 to 300 colonies, and above that was considered to be TNTC (too numerous to count).

(g) General Procedure for Wiping a Previously Inoculated Petri Dish Carrier with a Disinfectant Wet Wipe—Testing Contact Sanitizer/Disinfectant Efficacy 1. The indicated wet wipe was removed from its pouch and unfolded. The wipe was wrapped around both the index and middle fingers twice such that a 5 cm×5 cm area of the wet wipe was exposed.

2. The surface of the petri dish carrier was wiped from outer region to inner region and then back within about 6 seconds. The wipe was discarded.

3. Time was started with wiping. The petri dish carriers were left with their lids on for the remainder of testing period.

4. Following the prescribed time period, 20 ml D/E broth was added to the carrier and a scraper was used to dislodge attached bacteria. The broth was transferred to a 50 ml conical tube.

5. For control carriers, D/E broth was added on an inoculated carrier (pre-wipe), and an inoculated carrier wiped with sterile water (post-wipe) to determine the number of bacteria prior and post wipe.

6. 10-fold serial dilutions were prepared and plated on TSA plates. CFU counts were made between 30 to 300 colonies, and above that was considered to be TNTC (too numerous to count).

(h) General Procedure for Subjecting an Antimicrobial Coating to a Rinse Test

In various examples, microscope slide carriers previously coated with antimicrobial coatings delivered from a wet wipe and then dried were exposed to water to test if the coatings could survive wetting. The general procedure was as follows:

1. The test carriers were put into petri dishes and 20 ml of deionized water was added.
2. After 10 minutes (without shaking), the water was removed and slides were left to air dry overnight prior to residual antimicrobial efficacy testing.

(i) General Procedure for Subjecting an Antimicrobial Coating to Abrasion Testing In various examples, microscope slide carriers previously coated with antimicrobial coatings delivered from a wet wipe and then dried were exposed to mechanical abrasion in a straight-line washability machine (Gardco) to test if the coatings could survive mechanical wear, such as simulated frequent touching. The general procedure used was an adaption of EPA Protocol #01-1A, entitled "EPA Protocol for Residual Self-Sanitizing Activity of Dried Chemical Residues on Hard, Non-Porous Surfaces," developed by the Clorox Company. The modified protocol follows:

1. The wear testing was performed in batches of 10.
2. TexWipe® cotton wipers (VWR #TWTX309) and TexWipe® FoamWipe™ wipers (VWR #TWTX704, as a liner) were cut to the size appropriate for the weigh boat of the Gardco machine. 1 layer of cotton wiper and 1 layer of foam wiper were attached to a 1.0 kg weigh boat for each wear cycle.
3. The cotton wiper was attached to the abrasion apparatus and was sprayed with deionized water for 3 seconds with a Preval Sprayer from a distance of 50 cm, unless modified as specified in a particular example. Abrasion testing was performed immediately after moisturizing the wiper.
4. Abrasions were performed using a Gardco D16V Abrasion Tester. A "cycle" is defined herein as 1 cycle=2 passes of the weighted boat over the test carriers, there and back. The speed was set to 2.5 such that each cycle took ~4-5 seconds to complete. The number of cycles used in the various abrasion tests was 2×, 4×, 5×, 6×, 8×, or 10×, as indicated in the particular examples.
5. The TexWipe® cotton wiper was changed after each abrasion cycle.

(j) General Procedure for Visualizing Evenness of Antimicrobial Coatings Delivered from a Wet Wipe In various examples, microscope slides were wiped with various wet wipes to obtain an antimicrobial coating on the slide. Since the actives are quaternary ammonium species generally, staining with bromophenol blue provided a quick and simple qualitative assessment of how evenly a wet wipe could deliver a coating on a surface. As discussed herein, isopropanol improved spreading considerably of coating compositions delivered from a wet wipe, depending on the other components in the liquid composition and the particular amount of IPA used. The various drawing figures herein show black-and-white images of stained slides, wherein the darker areas correspond to what were actually blue areas from reaction of quaternary with bromophenol blue.

EXAMPLE IV

This example (internal study PR-98) measured contact disinfection/sanitization efficacy of a DMOD/CPTMS/triethanolamine composition, with and without non-silane quaternary disinfectant in the composition, delivered from a wet wipe. Petri dish carriers were used. To improve spreading of the liquid composition on the carrier, various levels of IPA were tried. The carriers were previously contaminated with *S. epidermidis* ATCC 12228 as per the above general procedure.

Six compositions were used to make three separate wet wipe articles. Each of the six compositions included 0.75 wt. % DMOD, 0.12 wt. % CPTMS and 0.045 wt. % triethanolamine, based on the total weight of the liquid composition. The variable ingredients across the six compositions were BTC®-1210 (present at 0.32 wt. % actives, or absent), and IPA (0, 25, or 50 wt. %), based on the total weight of the liquid composition. The compositions used were PR-98-1, PR-98-2, PR-98-3, PR-98-4, PR-98-5, and PR-98-6, as shown in TABLE 5. In each case, the wet wipe was prepared from the corresponding liquid composition in TABLE 5 and used as described above. The 0.32 wt. % actives BTC®-1210 comprised about 0.19 wt. % didecyldimethyl ammonium chloride and about 0.13 wt. % n-alkyl (50% C14, 40% C12, 10% C16) dimethylbenzyl ammonium chloride.

TABLE 5

Liquid Compositions for the Wet Wipes of Example IV

| | Weight Percent (actives) | | | | | |
| --- | --- | --- | --- | --- | --- | --- |
| Ingredient | PR-98-1 | PR-98-2 | PR-98-3 | PR-98-4 | PR-98-5 | PR-98-6 |
| DMOD | 0.75 | 0.75 | 0.75 | 0.75 | 0.75 | 0.75 |
| BTC ®-1210 | 0 | 0 | 0 | 0.32 | 0.32 | 0.32 |
| CPTMS | 0.12 | 0.12 | 0.12 | 0.12 | 0.12 | 0.12 |
| MTES | 0 | 0 | 0 | 0 | 0 | 0 |
| TEA | 0.045 | 0.045 | 0.045 | 0.045 | 0.045 | 0.045 |
| Isopropanol | 0 | 25 | 50 | 0 | 25 | 50 |
| Water | q.s 100.00 | q.s 100.00 | q.s 100.00 | q.s 100.00 | q.s 100.00 | q.s 100.00 |

The contact disinfection/sanitization results against *S. epidermidis* ATCC 12228 are shown in TABLE 6. The results for compositions PR-98-1, PR-98-2 and PR-98-3 indicate that wiping of DMOD antimicrobial wet wipes on inoculated surfaces provides effective reduction of bacteria by 3-logs, which is surprising to see with this antimicrobial that is more associated with bacteriostatic activity on dry surfaces. For these three compositions not containing a non-silane quaternary, addition of IPA seemed to have a negative effect on contact sanitization. For the wet wipes comprising both DMOD and a non-silane quaternary disinfectant, namely compositions PR-98-4, PR-98-5 and PR-98-6, the wet wipes were shown to effectively kill bacteria by more than 2.5 logs in 1 minute. Unlike the compositions absent non-silane quaternary, these wet wipes appeared to benefit from IPA in the liquid composition, wherein the addition of IPA increased spreading of the liquid from the wipe and increased kill up to 5 logs. The results in the table marked with an asterisk (*) indicate no growth at detection limit.

TABLE 6

Contact Disinfection/Sanitization against S. epidermidis ATCC 12228

| Contact Time | Wet Wipe Liquid | Geo. mean (CFU/mL) | $\text{Log}_{10}$ Reduction | Percent Reduction |
|---|---|---|---|---|
| 1 minute | Untreated (no wipe) | 4.03E+07 | — | — |
| | PR-98-1 | 2.00E+02 | 3.82 | 99.9995 |
| | PR-98-2 | 6.07E+04 | 1.33 | 99.85 |
| | PR-98-3 | 4.19E+04 | 1.49 | 99.90 |
| | PR-98-4 | 2.43E+03 | 2.73 | 99.994 |
| | PR-98-5 | 4.73E+02 | 3.44 | 99.999 |
| | PR-98-6 | 2.00E+01 | 4.82* | 99.99995* |
| 10 minutes | Untreated (wipe with H2O) | 1.31E+06 | — | — |
| | PR-98-1 | 7.75E+02 | 3.23 | 99.998 |
| | PR-98-2 | 3.47E+05 | 0.58 | 99.14 |
| | PR-98-3 | 2.00E+01 | 4.82* | 99.99995* |
| | PR-98-4 | 2.00E+01 | 4.82* | 99.99995* |
| | PR-98-5 | 2.00E+01 | 4.82* | 99.99995* |
| | PR-98-6 | 7.62E+01 | 4.24 | 99.9998 |

TABLE 7

Residual antimicrobial efficacy of surfaces previously coated with liquid coating composition delivered from a wet wipe

| Contact Time | Wet Wipe Liquid | Geo. mean (CFU/mL) | $\text{Log}_{10}$ Reduction | Percent Reduction |
|---|---|---|---|---|
| 1 minute | Untreated | 1.76E+07 | — | — |
| | PR-98-1 | 1.85E+07 | — | — |
| | PR-98-2 | 1.95E+07 | — | — |
| | PR-98-3 | 1.99E+07 | — | — |
| | PR-98-4 | 1.41E+06 | 1.10 | 92.01 |
| | PR-98-5 | 1.55E+06 | 1.06 | 91.21 |
| | PR-98-6 | 7.07E+04 | 2.40 | 99.60 |
| 10 minutes | Untreated | 1.76E+07 | — | — |
| | PR-98-1 | 1.65E+07 | — | — |
| | PR-98-2 | 1.89E+07 | — | — |
| | PR-98-3 | 1.99E+07 | — | — |
| | PR-98-4 | 2.35E+04 | 2.87 | 99.87 |
| | PR-98-5 | 7.56E+03 | 3.37 | 99.96 |
| | PR-98-6 | 2.00E+02 | 4.94* | 99.999* |
| 1 hour | Untreated (wipe with H2O) | 7.79E+06 | — | — |
| | PR-98-1 | 1.85E+06 | 0.62 | 76.27 |
| | PR-98-2 | 2.08E+06 | 0.57 | 73.30 |
| | PR-98-3 | 1.82E+06 | 0.63 | 76.63 |
| | PR-98-4 | 2.88E+02 | 4.43 | 99.996 |
| | PR-98-5 | 1.50E+03 | 3.72 | 99.98 |
| | PR-98-6 | 2.00E+01 | 5.59* | 99.9997* |

EXAMPLE V

This example (internal study PR-99) demonstrates the use of a wet wipe article to apply a residual antimicrobial coating on a carrier surface. As mentioned, wet wipe delivery of an antimicrobial coating provides a convenient alternative to spray coating. In this example, microscope slides were used as the carriers. The general procedures were followed, wherein microscope slide carriers were first coated by using a wet wipe to deliver the liquid coating composition, and then the dried coated carriers were tested for residual antimicrobial efficacy. The duration in which the S epidermidis culture remained in contact with the previously coated slides was 1 minute, 10 minutes, and 1 hour. The experiments also used the six compositions in TABLE 5 to produce the corresponding wet wipes.

The results are shown in TABLE 7. The results marked with an asterisk (*) indicate no growth at detection limit. The use of IPA impacted the coating of formulations on the glass carriers. 25 wt. % IPA in the liquid composition did not increase the evenness of the DMOD/CPTMS/triethanolamine coating, except if the base composition also included the non-silane quaternary. However, 50% IPA increased the evenness of a DMOD/CPTMS/triethanolamine coating with or without non-silane quaternary.

The coating derived from a wet wipe comprising DMOD/CPTMS/triethanolamine was not effective in killing bacteria. Further, the addition of IPA, shown to increase distribution of the coating, did not have any effects. However, a wet wipe comprising DMOD/CPTMS/triethanolamine and non-silane quaternary provided a coating that was effective at almost 3 logs in 10 minutes. The addition of IPA increased the distribution and may have attributed to the increased kill of bacteria to almost 5 logs in 10 minutes. This result is entirely unexpected since non-silane quaternary ammonium compounds are not known to form residual antimicrobial coatings but instead are known for contact disinfection. It is possible that the DMOD and/or CPTMS are polymerizing on the surface and trapping the non-silane quaternary thereon. The IPA is key to even spreading, and the non-silane quaternary is key to high residual antimicrobial efficacy from the dried coating.

Figure 6:
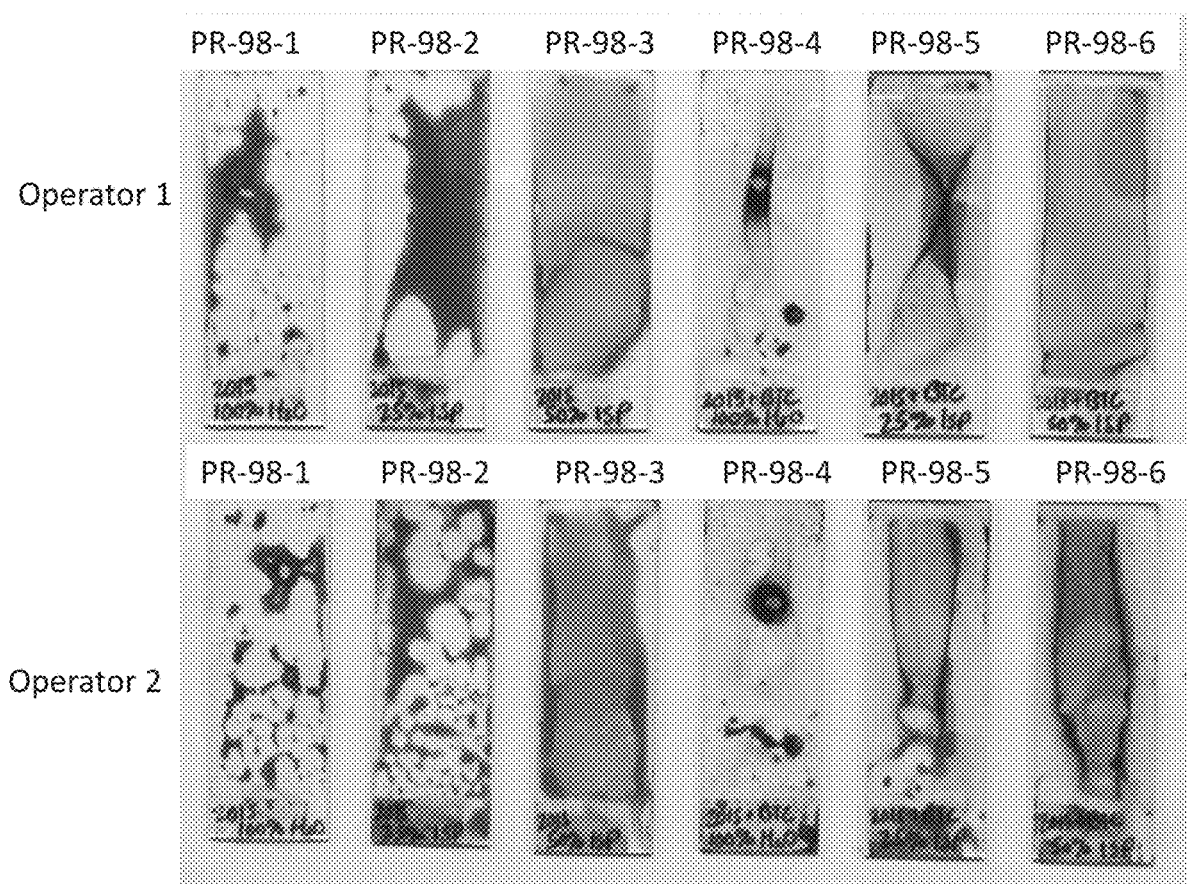
FIG. 6 shows black and white images of bromophenol blue stained microscope slides that illustrate wetting and spreading of various compositions on a glass surface and variation between operators.

FIG. 6 illustrates various test slides from this example after staining with bromophenol blue. These staining tests show the improvement in evenness achieved with added IPA but also show user variability between the upper row of slides coated by "Operator 1" and the lower row of slides coated by "Operator 2."

EXAMPLE VI

This example (internal study PR-101) was conducted to determine the antimicrobial efficacy of DMOD based coatings delivered from a wet wipe, with and without non-silane quaternary, with increased CPTMS and with IPA at 0 wt. %, 50 wt. %, or 60 wt. %. In particular, 60 wt. % IPA was investigated for further increases in efficacy and better spreading. IPA would be expected to fully evaporate from the coated surface at room temperature, and thus not be expected to contribute to residual antimicrobial efficacy per se. However, it remains at least possible that improved wetting and spreading of a coating composition indirectly improves residual antimicrobial efficacy because it is more likely the inoculum will come in contact with coated rather than uncoated surface.

This example includes both residual antimicrobial efficacy testing on coated surfaces and contact disinfection of previously contaminated surfaces using a wet wipe. As in the previous example, the general procedure was followed where glass microscope slides were coated with coating compositions delivered from a wet wipe and then allowed to dry overnight before testing residual antimicrobial efficacy. In the second part of the example, glass petri dish carriers were first inoculated prior to testing contact disinfection efficacy from a wet wipe.

The liquid compositions used to produce the wet wipes of EXAMPLE VI are shown in TABLE 8. The general procedures described above were followed for making the wet wipes, coating the slides and testing residual antimicrobial efficacy.

TABLE 8

Liquid Compositions for the Wet Wipes of Example VI

| Ingredient | Weight Percent (actives) | | | | | |
|---|---|---|---|---|---|---|
| | PR-101-1 | PR-101-2 | PR-101-3 | PR-101-4 | PR-101-5 | PR-101-6 |
| DMOD | 0.75 | 0.75 | 0.75 | 0.75 | 0.75 | 0.75 |
| BTC ®-1210 | 0 | 0 | 0 | 0.32 | 0.32 | 0.32 |
| CPTMS | 0.26 | 0.26 | 0.26 | 0.26 | 0.26 | 0.26 |
| MTES | 0 | 0 | 0 | 0 | 0 | 0 |
| TEA | 0.045 | 0.045 | 0.045 | 0.045 | 0.045 | 0.045 |
| Isopropanol | 0 | 50 | 60 | 0 | 50 | 60 |
| Water | q.s 100.00 | q.s 100.00 | q.s 100.00 | q.s 100.00 | q.s 100.00 | q.s 100.00 |

TABLE 9 shows the results of the residual antimicrobial efficacy testing on previously coated microscope slide carriers inoculated with *S. epidermidis*.

TABLE 9

Residual antimicrobial efficacy of surfaces previously coated with liquid coating composition delivered from a wet wipe

| Contact Time | Wet Wipe Liquid | Geo. mean (CFU/mL) | $Log_{10}$ Reduction | Percent Reduction |
|---|---|---|---|---|
| Time Zero | Untreated | 1.46E+07 | — | — |
| 30 seconds | PR-101-4 | 6.54E+06 | 0.35 | 55.26 |
| | PR-101-5 | 2.61E+06 | 0.75 | 82.14 |
| | PR-101-6 | 2.65E+06 | 0.74 | 81.87 |
| 2 minutes | PR-101-4 | 2.59E+05 | 1.75 | 98.23 |
| | PR-101-5 | 1.35E+05 | 2.04 | 99.08 |
| | PR-101-6 | 7.43E+04 | 2.29 | 99.49 |
| 5 minutes | PR-101-4 | 1.12E+05 | 2.12 | 99.24 |
| | PR-101-5 | 3.17E+04 | 2.66 | 99.78 |
| | PR-101-6 | 7.27E+03 | 3.30 | 99.95 |
| 10 minutes | PR-101-4 | 4.35E+04 | 2.53 | 99.70 |
| | PR-101-5 | 6.12E+03 | 3.38 | 99.96 |
| | PR-101-6 | 1.79E+02 | 4.91 | 99.999 |
| 1 hour | Untreated | 1.52E+07 | — | — |
| | PR-101-1 | 8.32E+06 | 0.26 | 45.40 |
| | PR-101-2 | 6.07E+06 | 0.40 | 60.15 |
| | PR-101-3 | 7.17E+06 | 0.33 | 52.89 |
| 4 hours | Untreated | 1.37E+07 | — | — |
| | PR-101-1 | 7.6E+06 | 0.26 | 44.57 |
| | PR-101-2 | 5.91E+06 | 0.37 | 56.87 |
| | PR-101-3 | 5.39E+06 | 0.41 | 60.72 |

Figure 7:
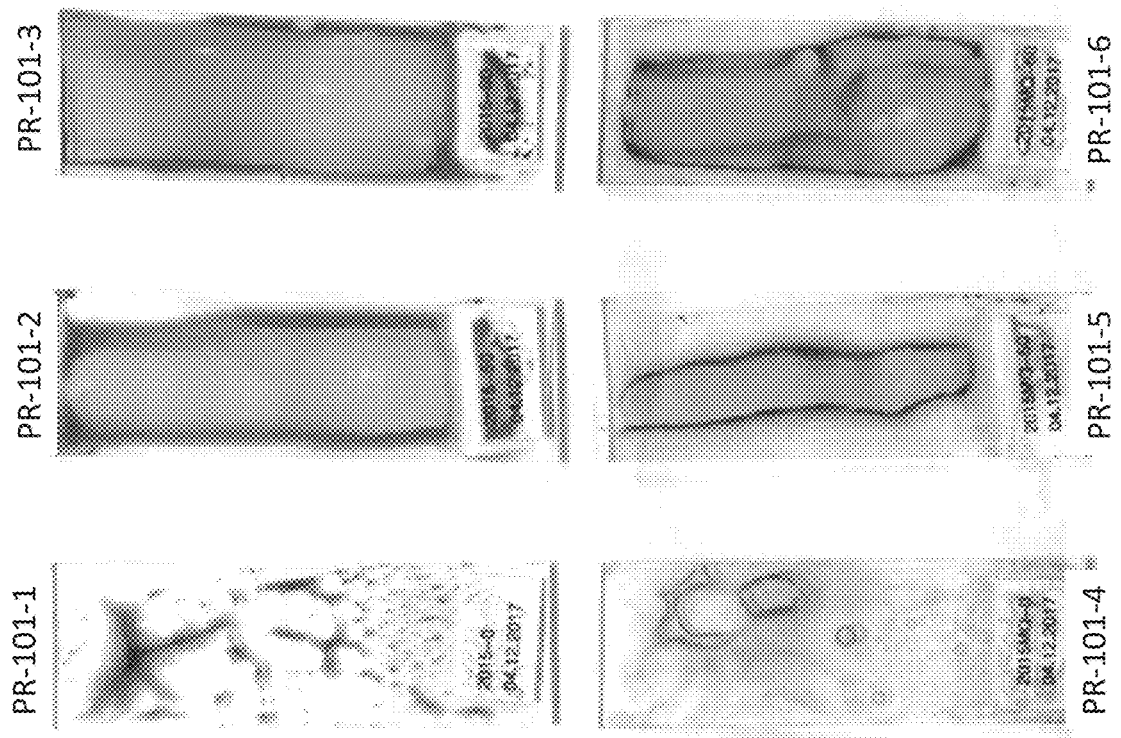
FIG. 7 shows black and white images of bromophenol blue stained microscope slides that illustrate wetting and spreading of various compositions on a glass surface.
Figure 8:
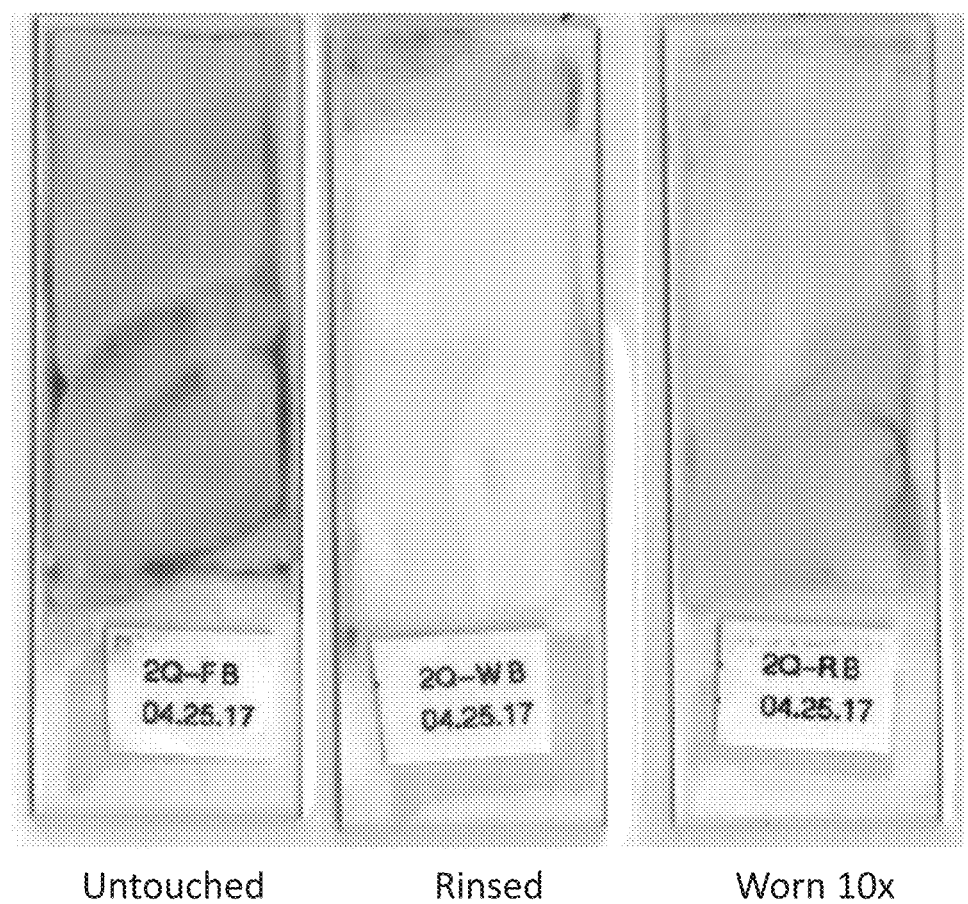
FIG. 8 shows black and white images of bromophenol blue stained microscope slides that illustrate wetting and spreading of various compositions on a glass surface.

The results show a clear trend of increased residual antimicrobial efficacy with increasing amounts of IPA for surfaces coated with compositions comprising DMOD and non-silane quaternary. The increasing antimicrobial efficacy correlates with the improved spreading, as shown in FIG. 7. FIG. 7 shows the improvement in spreading seen from PR-101-1 to PR-101-2 to PR-101-3 (increasing IPA in the compositions not including non-silane quaternary), and the improvement in spreading seen from PR-101-4 to PR-101-5 to PR-101-6 (increasing IPA in the compositions that included non-silane quaternary). The PR-101-6 coating exhibited the highest residual antimicrobial efficacy, the coating that included non-silane quaternary and exhibited improved wetting and spreading provided by the 60 wt. % IPA.

The second portion of EXAMPLE VI studied the contact sanitization/disinfection strength of various wet wipes against *S. epidermidis* previously inoculated on a surface. Wet wipes derived from the liquid compositions of TABLE 8 were also used for this portion of the study. The generalized procedures above were followed. The contact sanitization/disinfectant results are set forth in TABLE 10. The results marked with an asterisk (*) indicate no growth at detection limit.

TABLE 10

Contact Disinfection/Sanitization against *S. epidermidis* ATCC 12228

| Contact Time | Wet Wipe Liquid | Geo. mean (CFU/mL) | $Log_{10}$ Reduction | Percent Reduction |
|---|---|---|---|---|
| Time Zero | Untreated (no wipe) | 7.81E+07 | — | — |
| | Untreated (wipe with $H_2O$) | 6.24E+05 | — | — |
| 30 seconds | Control (50% IPA) | 2.00E+02 | 3.49 | 99.97 |
| | Control (60% IPA) | 2.00E+02 | 3.49 | 99.97 |
| | PR-101-1 | 8.10E+03 | 1.89 | 98.70 |
| | PR-101-2 | 2.83E+02 | 3.34 | 99.95 |
| | PR-101-3 | 2.00E+02 | 3.49 | 99.97 |
| | PR-101-4 | 2.00E+02 | 3.49 | 99.97 |
| | PR-101-5 | 2.00E+02 | 3.49 | 99.97 |
| | PR-101-6 | 3.74E+02 | 3.22 | 99.94 |
| 2 minutes | Control (50% IPA) | 2.00E+02 | 3.49 | 99.97 |
| | Control (60% IPA) | 3.16E+02 | 3.30 | 99.95 |
| | PR-101-1 | 3.32E+02 | 3.27 | 99.95 |
| | PR-101-2 | 2.00E+01 | 4.49* | 99.997* |
| | PR-101-3 | 2.00E+01 | 4.49* | 99.997* |
| | PR-101-4 | 2.00E+01 | 4.49* | 99.997* |
| | PR-101-5 | 2.00E+01 | 4.49* | 99.997* |
| | PR-101-6 | 2.00E+01 | 4.49* | 99.997* |

As shown by the results, the wet wipes performed well, achieving >3 log reduction in *S. epidermidis* in 2 minutes even without IPA. Since IPA does function as a contact disinfectant, addition of IPA increased kill and no bacteria at all could be detected at 2 minutes. In both portions of the example, it is clear that 60% IPA increased spreading of coating composition, consequently improving residual sanitizing, and increased killing effect when the wipe was used as a disinfecting wipe. The liquid composition PR-101-6 is an ideal formulation for a wet wipe that can function as both a contact disinfecting wipe and a wet wipe for applying an antimicrobial coating to a surface.

EXAMPLE VII

This example (internal study PR-103) was conducted to determine if antimicrobial coatings delivered from a wet wipe maintained residual antimicrobial activity after rinsing or abrasion of the coated surface. The abrasion testing was modified by spraying from a shorter distance (50 cm instead of 75 cm) and a longer spray time (3 seconds instead of 2 seconds). The rinsing test was modified by rinsing for 10 minutes without shaking instead of 30 minutes with shaking. The general rinsing and abrasion testing procedures above reflect these modifications.

To compare wet wipe compositions based on DMOD to compositions only including non-silane quaternary disinfectants, glass slides were wiped with either a DMOD/non-silane quaternary composition having 60% IPA, (PR-103-1 in TABLE 11, which is the same composition as PR-101-6 in TABLE 8), or a "free quat" composition, (PR-103-2 in TABLE 11), which only consists of the non-silane quaternary BTC®-1210 and 60% IPA as the actives, remainder water. The wet wipes were prepared from these liquid compositions per the general procedures above. All testing was also per the generalized procedures. The coated slides were dried, used as is (indicated as "fresh"), subjected to the rinsing protocol (indicated as "rinsed") or subjected to the abrasion protocol (indicated as "worn 10×"), and then tested against *S. epidermidis*, with neutralization and plating after the indicated time points.

TABLE 11

Liquid Compositions for the Wet Wipes of Example VII

| Ingredient | Weight Percent (actives) | |
|---|---|---|
| | PR-103-1 | PR-103-2 |
| DMOD | 0.75 | 0 |
| BTC ®-1210 | 0.32 | 0.32 |
| CPTMS | 0.26 | 0 |
| MTES | 0 | 0 |
| TEA | 0.045 | 0 |
| Isopropanol | 60 | 60 |
| Water | q.s 100.00 | q.s 100.00 |

The residual antimicrobial efficacy results are shown in TABLE 12. The results marked with an asterisk (*) indicate no growth at detection limit. FIG. 9 shows bromophenol blue staining of PR-103-1 coated slides. The untouched slide shows the remarkable evenness of the coating composition delivered from the wet wipe. However, the rinsed slide shows very little quaternary, and the 10× worn slide shows substantial reduction in the coating. The results show that although untouched coatings from PR-103-1 and PR-103-2 wet wipes eliminated bacteria inoculated on the surface, abrasion (10×) or rinsing (10 min in water) removed much of the coatings, and even after 4 hours of contact time between the inoculum and the remaining coating, neither could achieve 1 log kill.

TABLE 12

Residual antimicrobial efficacy of surfaces previously coated with liquid coating composition delivered from a wet wipe

| Contact Time | Wet Wipe Liquid. | Condition | Geo. mean (CFU/mL) | $Log_{10}$ Reduction | Percent Reduction |
|---|---|---|---|---|---|
| 5 minutes | Untreated | | 1.5E+06 | — | — |
| | PR-103-1 | Fresh | 3.6E+02 | 3.62 | 99.98 |
| | | Worn 10× | 1.6E+06 | — | — |
| | | Rinsed | 1.8E+06 | — | — |
| | PR-103-2 | Fresh | 2.9E+01 | 4.71 | 99.998 |
| | | Worn 10× | 5.4E+05 | 0.44 | 63.35 |
| | | Rinsed | 1.6E+06 | — | — |
| 30 minutes | Untreated | | 8.6E+05 | — | — |
| | PR-103-1 | Fresh | 1.1E+02 | 3.88 | 99.99 |
| | | Worn 10× | 1.1E+05 | 0.89 | 87.22 |
| | | Rinsed | 5.3E+04 | 1.21 | 93.77 |
| | PR-103-2 | Fresh | 3.3E+01 | 4.41 | 99.996 |
| | | Worn 10× | 3.8E+05 | 0.36 | 55.92 |
| | | Rinsed | 2.8E+05 | 0.49 | 67.35 |
| 4 hours | Untreated | | 1.1E+06 | — | — |
| | PR-103-1 | Fresh | 2.0E+01 | 4.75* | 99.998* |
| | | Worn 10× | 2.9E+05 | 0.59 | 74.49 |
| | | Rinsed | 8.6E+05 | 0.12 | 23.91 |
| | PR-103-2 | Fresh | 3.6E+01 | 4.50 | 99.997 |
| | | Worn 10× | 2.1E+05 | 0.74 | 81.67 |
| | | Rinsed | 3.2E+05 | 0.56 | 72.21 |

EXAMPLE VIII

This example (internal study PR-107) compared various wet wipes of the present disclosure to a commercially available disinfectant wipe having no claims to residual antimicrobial efficacy. The comparative product was Super Sani-Cloth® from Nice-Pak/PDI, Inc., Orangeburg, N.Y. The MSDS for this disinfecting wipe indicates that the liquid composition in the wipe contains 55 wt. % IPA, 0.25 wt. % alkyl (60% C14, 32% C16, 5% C12, 5% C18) dimethylbenzyl ammonium chloride and 0.25 wt. % alkyl (68% C12, 32% C14) dimethyl ethylbenzyl ammonium chloride, (thus a total of 0.5 wt. % active non-silane quaternary). The wipes of the present disclosure were adjusted to also include 0.5 wt. % total non-silane quaternary actives in addition to the DMOD actives, to make this comparison more meaningful.

TABLE 13 sets forth the liquid compositions used to for the wet wipes in this study. This example also studied increasing the DMOD concentration from 0.75 to up to 3.0 wt. % actives. CPTMS was increased proportionally to the DMOD since this material provided formula stability. The mixture of BTC®-1210; BTC®-2125M; BTC®-1010 used provided 0.27 wt. % didecyldimethyl ammonium chloride, 0.07 wt. % n-alkyl (50% C14, 40% C12, 10% C16) dimethyl benzyl ammonium chloride, 0.08 wt. % n-alkyl (60% C14, 30% C16, 5% C12, 5% C18) dimethyl benzyl ammonium chloride and 0.80 wt. % n-alkyl (68% C12, 32% C14) dimethyl ethylbenzyl ammonium chloride. Each one of the coated slides was subjected to 5× cycles of abrasion prior to efficacy testing.

TABLE 13

Liquid Compositions for the Wet Wipes of Example VIII

| Ingredient | Weight percent (actives) | | |
|---|---|---|---|
| | PR-107-1 | PR-107-2 | PR-107-3 |
| DMOD | 0.75 | 1.50 | 3.00 |
| BTC ®-1210; BTC ®-2125M; BTC ®-1010 | 0.50 | 0.50 | 0.50 |
| CPTMS | 0.26 | 0.40 | 0.68 |
| MTES | 0 | 0 | 0 |
| TEA | 0.045 | 0.045 | 0.045 |
| Isopropanol | 60 | 60 | 60 |
| Water | q.s 100.00 | q.s 100.00 | q.s 100.00 |

The results are shown below in TABLE 14. As shown, PR-107-3 delivered from a wet wipe can exceed 1.5 log kill after 4 hours, while the commercial disinfectant wipes could only reach 0.5 log kill. Further, there is a dramatic increase in residual antimicrobial efficacy when increasing the DMOD from 1.5 wt. % actives to 3.0 wt. % actives.

TABLE 14

Residual antimicrobial efficacy of surfaces previously coated with liquid coating composition delivered from a wet wipe

| Contact Time | Wet Wipe Liquid | Condition | Geo. mean (CFU/mL) | $Log_{10}$ Reduction | Percent Reduction |
|---|---|---|---|---|---|
| 10 minutes | Untreated | | 1.8E+06 | — | — |
| | PR-107-1 | Worn 5× | 1.6E+06 | 0.06 | 12.4 |
| | PR-107-2 | Worn 5× | 1.7E+06 | 0.03 | 6.3 |
| | PR-107-3 | Worn 5× | 9.3E+04 | 1.28 | 94.8 |
| | Super Sani-Cloth ® | Worn 5× | 1.1E+06 | 0.21 | 38.4 |
| 1 hour | Untreated | | 1.7E+06 | — | — |
| | PR-107-1 | Worn 5× | 1.5E+06 | 0.05 | 10.7 |
| | PR-107-2 | Worn 5× | 1.6E+06 | 0.05 | 10.0 |
| | PR-107-3 | Worn 5× | 4.6E+04 | 1.57 | 97.3 |
| | Super Sani-Cloth ® | Worn 5× | 6.7E+05 | 0.41 | 61.4 |
| 4 hours | Untreated | | 1.8E+06 | — | — |
| | PR-107-1 | Worn 5× | 7.3E+05 | 0.39 | 59.7 |
| | PR-107-2 | Worn 5× | 7.1E+05 | 0.41 | 61.0 |
| | PR-107-3 | Worn 5× | 4.2E+04 | 1.63 | 97.7 |
| | Super Sani-Cloth ® | Worn 5× | 4.7E+05 | 0.58 | 74.0 |

Figure 9A:
FIG. 9A-FIG. 9C show black and white images of bromophenol blue stained microscope slides that illustrate wetting and spreading of various compositions on a glass surface.
Figure 9B:
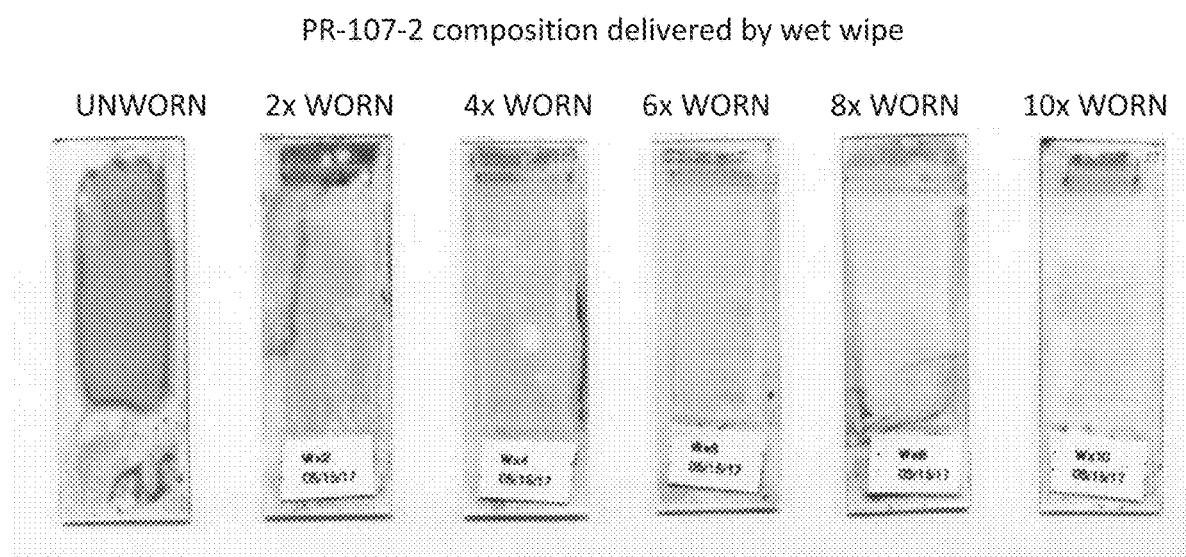
Figure 9C:
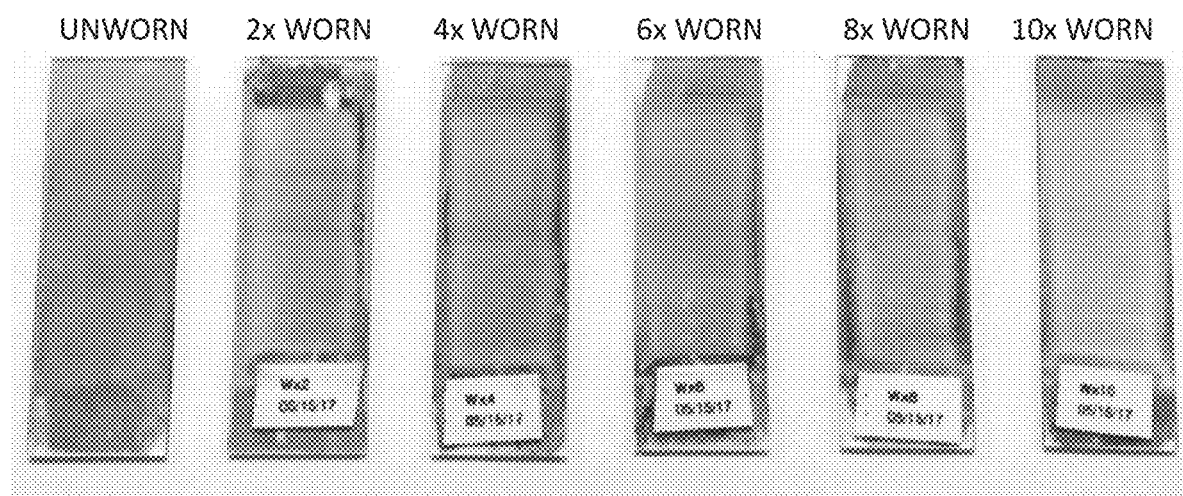

FIGS. 9A-9C show bromophenol blue stained slides for the coatings derived from PR-107-1 (FIG. 9A), PR-107-2 (FIG. 9B) and PR-107-3 (FIG. 9C), for 2×, 4×, 6×, 8×, and 10× cycles of abrasion in the abrasion tester. As shown in FIG. 9C, a coating of PR-107-3 composition delivered from a wet wipe is remarkably even coated, and unexpectedly durable. Even after 10 wear cycles in the abrasion tester, the PR-107-3 coating remains substantially intact.

EXAMPLE IX

This example (internal study PR-125) looked at the ability of coatings delivered from a wet wipe to withstand repeated abrasion and inoculation. For this purpose, a schedule was devised to simulate the repeated handling and contamination of a surface that may be seen in a public setting, such as in a hospital. It was previously shown in EXAMPLE VIII that a coating comprising 3 wt. % active DMOD, delivered from a wet wipe, is remarkably durable toward mechanical abrasion.

For this example, the wet wipes used were produced from the liquid composition PR-125-1 shown in TABLE 15, per the general procedures above for impregnating the nonwoven substrate. The mixture of BTC®-1210; BTC®-2125M; BTC®-1010 used provided 0.27 wt. % didecyldimethyl ammonium chloride, 0.07 wt. % n-alkyl (50% C14, 40% C12, 10% C16) dimethyl benzyl ammonium chloride, 0.08 wt. % n-alkyl (60% C14, 30% C16, 5% C12, 5% C18) dimethyl benzyl ammonium chloride and 0.80 wt. % n-alkyl (68% C12, 32% C14) dimethyl ethylbenzyl ammonium chloride, based on the total weight of the liquid composition, as in EXAMPLE VIII. In liquid composition PR-125-1, a new stabilizer is introduced, methyltriethoxysilane, (referred to herein as "MTES"). MTES appears to stabilize DMOD compositions similar to CPTMS. That is, MTES prevents formula instability, such as cloudiness and precipitation over time. Although a known use of MTES is to make surfaces less polar, by bonding MTES onto the surface whereby only the non-polar methyl groups append from the surface, it appears that use of MTES to stabilize liquid compositions comprising DMOD and non-silane quaternary ammonium chlorides has not been described previously. No theory is proffered for the ability of MTES to stabilize a liquid composition of DMOD in this way.

Coatings of the PR-125-1 composition delivered from a wet wipe onto microscope slides measured about 0.488 mg±0.124 mg per slide. The microscope slide carriers used herein measured 1"×3", or 3 sq. inches. Therefore, the PR-125-1 coatings delivered from the nonwoven wet wipe weigh about 0.163 mg/sq. inch of surface area.

TABLE 15

Liquid Compositions for the Wet Wipes of Example VIII

| Ingredient | Weight percent (actives) PR-125-1 |
|---|---|
| DMOD | 3.00 |
| BTC ®-1210; BTC ®-2125M; BTC ®-1010 | 0.50 |
| CPTMS | 0.56 |
| MTES | 0.11 |
| TEA | 0.045 |
| Isopropanol | 60 |
| Water | q.s. 100.00 |

For the residual sanitizer testing, the coated microscope slide carriers were inoculated 5-times with *S. epidermidis* ATTC 12228 between 12 alternating dry and wet wear cycles on the abrasion tester. The sanitizer test was performed against *S. epidermidis*, and quantified by pour plating General Procedures Used for Example IX:

Day 1: Carrier Inoculation and Antimicrobial Coating Application Via a Wet Wipe (PR-125-1)

1. For the initial inoculations, a 24 hour culture of *S. epidermidis* ATCC 12228 was initiated in tryptic soy broth at 37° C. The culture was diluted 1:10000 in deionized $H_2O$.

2. Total of 24 sterile glass slides were placed flat in Petri dishes lined with 2 layers of paper towel underneath.

3. The slides were inoculated with *S. epidermidis* (0.010 ml) pipetted onto the center, and spread over a surface area of 1 sq. inch using a sterile, bent pipette tip, and dried uncovered (25° C., 45-55% Relative Humidity) for 30 minutes.

4. Twelve of the inoculated slides were wiped with the wet wipe: a. PR-125-1 wet wipes were removed aseptically from bags, unfolded, and wrapped around the index and middle finger twice to expose a 5 cm×5 cm area; b. Slides were removed from petri dishes and held firmly against the rim; c. Wipes were firmly streaked on the carrier back and forth 3 times (total 6 passes) in 5 seconds, and slides were placed in their individual dishes and left undisturbed to cure at 25° C. for 24 hours.

5. After the slides were dry: a. Four coated slides were left aside and labeled as fresh (PR-125-1 coated, but not subjected to wearing/re-inoculations); b. Eight slides were labeled as worn (PR-125-1 coated, and subjected to wearing/re-inoculations).

6. The remaining 12 slides were labeled as untreated (not coated, not worn).

Day 2: Carrier Re-inoculations and Wearing

1. For the re-inoculations, fresh 18-24 h cultures were diluted 1:20000 in deionized $H_2O$ with 5% FBS.

2. The slides were reinoculated and worn 5 times with alternating dry and wet cycles as specified in Table 16.

Day 3—Carrier Wearing and Sanitizer Test

1. The slides were worn with alternating dry and wet cycles as specified in Table 16.

2. For the final re-inoculation, fresh 18-24 h culture was diluted 1:20 in deionized $H_2O$ with 5% FBS.

3. Slides (including untreated and fresh) were inoculated with the final re-inoculation (25° C., 50% Relative Humidity) described above.

4. After contact time, the slides were transferred to 25 ml of letheen broth in conical tubes and vortexed for 2 min.

5. The PR-125-1 coated carriers were serially plated by pour plating $10^0$ to $10^{-2}$ in tryptic soy agar. Control carriers were serially diluted in PBS and plated at $10^{-3}$ and $10^{-4}$.

6. The plates were inverted and incubated at 37° C. for 48 hours, and plates containing between 30 and 300 CFU recorded.

7. $Log_{10}$ and percent reductions were calculated relative to the timed control bacterial counts.

TABLE 16

Three-day abrasion, re-inoculation and sanitizer procedure

| DAY 1 | Inoculation of all carriers with initial inoculation culture Test/control composition application via wet wipe and drying |
|---|---|
| DAY 2 | Dry abrasion (wear #1) Re-inoculation 1* |

TABLE 16-continued

Three-day abrasion, re-inoculation and sanitizer procedure

|       |                         |
|-------|-------------------------|
|       | Wet abrasion (wear #2)  |
|       | Re-inoculation 2*       |
|       | Dry abrasion (wear #3)  |
|       | Re-inoculation 3*       |
|       | Wet abrasion (wear #4)  |
|       | Re-inoculation 4*       |
|       | Dry abrasion (wear #5)  |
|       | Re-inoculation 5*       |
| DAY 3 | Wet abrasion (wear #6)  |
|       | Dry abrasion (wear #7)  |
|       | Wet abrasion (wear #8)  |
|       | Dry abrasion (wear #9)  |
|       | Wet abrasion (wear #10) |
|       | Dry abrasion (wear #11) |
|       | Wet abrasion (wear #12) |
|       | SANITIZATION TEST       |

*indicates "with re-inoculation culture"

The results are shown in TABLE 17. The detection limit was 1 bacterium in 25 mL letheen broth=$2.5 \times 10^1$ CFU/mL. In the table, "Fresh" indicates PR-125-1 coated carriers not subjected to any abrasion or re-inoculations, and "worn" indicates PR-125-1 coated carriers subjected to the abrasion/re-inoculation schedule.

TABLE 17

Residual antimicrobial efficacy of surfaces previously coated with liquid coating composition PR-125-1 delivered from a wet wipe and subjected to alternating wear/inoculation

| Contact Time | Condition | Geo. mean (CFU/mL) | $Log_{10}$ Reduction | Percent Reduction |
|---|---|---|---|---|
| Time Zero | Untreated | 7.50E+05 | — | — |
|  | Untreated | 4.99E+05 | — | — |
| 1 hour | Fresh | 2.50E+01 | 4.3 | 99.99 |
|  | Worn | 1.30E+02 | 3.58 | 99.97 |
| 2 hours | Untreated | 6.50E+05 | — | — |
|  | Worn | 4.88E+02 | 3.12 | 99.92 |

As shown in TABLE 17, at 1 hour contact time, PR-125-1 as delivered from a wet wipe can kill>99,9% *S. epidermidis* even if the coating on the surface is subjected to an aggressive wet and dry abrasion and re-inoculation schedule.

It has been demonstrated that a wet wipe can provide both contact sanitization/disinfection against germs present on a surface and residual antimicrobial efficacy against germs later transferred to that surface. Wiping a surface with a wet wipe impregnated with a liquid provides an alternative to spray coating the surface. In this way, inhalation issues associated with high levels of quaternary are eliminated.

In various embodiments, a wet wipe comprises a nonwoven substrate and a liquid composition impregnated therein, the liquid composition comprising dimethyloctadecyl[3-(trimethoxysilyl)propyl] ammonium chloride, at least one non-silane quaternary disinfectant, triethanolamine, 3-chloropropyltrimethoxysilane, methyltriethoxy silane, and isopropanol, remainder water.

Antimicrobial wet wipes, methods of making wet wipes and methods of using same are provided. References to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a molecule, composition, process, method, or device that comprises a list of elements does not include only those elements but may include other elements not expressly listed or inherent to such molecules, compositions, processes, methods, or devices.

We claim:

1. A wet wipe comprising:
   (a) a substrate; and
   (b) a liquid composition impregnated therein, the liquid composition comprising:
      (i) at least one organosilane;
      (ii) at least one non-silane quaternary disinfectant;
      (iii) triethanolamine; and
      (iv) a solvent.

2. The wet wipe of claim 1, wherein the at least one organosilane comprises dimethyloctadecyl[3-(trimethoxysilyl)propyl] ammonium chloride.

3. The wet wipe of claim 1, wherein the liquid composition further comprises at least one of 3-chloropropyltrimethoxysilane and methyltriethoxysilane.

4. The wet wipe of claim 1, wherein the at least one non-silane quaternary disinfectant is selected from the group consisting of n-alkyldimethylbenzyl ammonium chlorides, didecyldimethyl ammonium chlorides, n-alkyl dimethylethylbenzyl ammonium chlorides, dialkyldimethyl ammonium chlorides, and mixtures thereof.

5. The wet wipe of claim 1, wherein the solvent comprises aqueous isopropanol.

6. The wet wipe of claim 1, wherein the at least one organosilane comprises a mixture of dimethyloctadecyl[3-(trimethoxysilyl)propyl] ammonium chloride and 3-chloropropyltrimethoxysilane.

7. The wet wipe of claim 1, wherein at least one organosilane comprises a mixture of dimethyloctadecyl[3-(trimethoxysilyl)propyl] ammonium chloride, 3-chloropropyltrimethoxysilane and methyltriethoxysilane.

8. The wet wipe of claim 1, wherein the substrate comprises a woven or nonwoven fabric, or a porous plastic sheet comprising sintered plastic particles.

9. A wet wipe comprising:
(a) a substrate comprising woven fabric, nonwoven fabric or a sheet of porous plastic; and
(b) an aqueous liquid composition impregnated therein, the liquid composition comprising:
(i) from about 0.1 wt. % to about 5 wt. % organosilane, based on the total weight of the aqueous liquid composition;
(ii) from about 0.001 wt. % to about 1 wt. % non-silane quaternary disinfectant, based on the total weight of the aqueous liquid composition;
(iii) from about 0.001 wt. % to about 3 wt. % triethanolamine, based on the total weight of the aqueous liquid composition; and
(iv) from about 40 wt. % to about 80 wt. % isopropanol, based on the total weight of the aqueous liquid composition.

10. The wet wipe of claim 9, wherein the organosilane comprises from about 0.75 wt. % to about 3 wt. % dimethyloctadecyl[3-(trimethoxysilyl)propyl] ammonium chloride, based on the total weight of the aqueous liquid composition.

11. The wet wipe of claim 10, wherein the organosilane further comprises at least one of 3-chloropropyltrimethoxysilane and methyltriethoxysilane.

12. The wet wipe of claim 9, wherein the non-silane quaternary disinfectant comprises from about 0.3 wt. % to about 0.5 wt. % of a mixture of didecyldimethyl ammonium chloride, n-alkyl (50% C14, 40% C12, 10% C16) dimethyl benzyl ammonium chloride, n-alkyl (60% C14, 30% C16, 5% C12, 5% C18) dimethyl benzyl ammonium chloride and n-alkyl (68% C12, 32% C14) dimethyl ethylbenzyl ammonium chloride, based on the total weight of the aqueous liquid composition.

13. A method for providing contact sanitization of a surface and for coating the surface with a residual antimicrobial coating, the method comprising:
wiping the surface with a wet wipe comprising: (a) a substrate; and (b) an aqueous liquid composition impregnated therein, the aqueous liquid composition comprising: (i) from about 0.75 wt. % to about 3.0 wt. % dimethyloctadecyl[3-(trimethoxysilyl)propyl] ammonium chloride, based on the total weight of the aqueous liquid composition; (ii) from about 0.3 wt. % to about 0.5 wt. % of a mixture of didecyldimethyl ammonium chloride, n-alkyl (50% C14, 40% C12, 10% C16) dimethyl benzyl ammonium chloride, n-alkyl (60% C14, 30% C16, 5% C12, 5% C18) dimethyl benzyl ammonium chloride and n-alkyl (68% C12, 32% C14) dimethyl ethylbenzyl ammonium chloride, based on the total weight of the aqueous liquid composition; (iii) from about 0.02 to about 0.06 wt. % triethanolamine, based on the total weight of the aqueous liquid composition; and (iv) from about 40 wt. % to about 80 wt. % isopropanol, based on the total weight of the aqueous liquid composition; and
allowing the surface to dry overnight,
wherein wiping delivers the aqueous liquid composition onto the surface to sanitize the surface and the aqueous liquid composition dries on the surface to form the residual antimicrobial coating.

14. The method of claim 13, wherein the substrate comprises a rayon/polyester blend nonwoven having a basis weight of less than about 10 osy.

15. The method of claim 13, wherein the aqueous liquid composition further comprises both 3-chloropropyltrimethoxysilane and methyltriethoxysilane, at a total amount of less than about 1 wt. %, based on the total weight of the aqueous liquid composition.

16. The method of claim 13, wherein the substrate comprises about 12-15 wt. % of the wet wipe, and the aqueous liquid composition comprises about 85-88 wt. % of the wet wipe, based on the total weight of the wet wipe.

17. The method of claim 13, wherein the aqueous liquid composition comprises about 60 wt. % isopropanol, based on the total weight of the aqueous liquid composition.

18. The method of claim 13, wherein the residual antimicrobial coating, after being exposed to a three-day abrasion/re-inoculation procedure, exhibits a greater than 99.9% kill of *S. epidermidis* 1 hour after inoculation of the coating with *S. epidermidis*.

19. The wet wipe of claim 1, wherein the at least one organosilane is present at from about 0.1 wt. % to about 5 wt. %, based on the total weight of the liquid composition.

20. The wet wipe of claim 1, wherein the at least one non-silane quaternary disinfectant is present at from about 0.001 wt. % to about 1 wt. %, based on the total weight of the liquid composition.

21. The wet wipe of claim 1, wherein the triethanolamine is present at from about 0.001 wt. % to about 3 wt. %, based on the total weight of the liquid composition.

22. The wet wipe of claim 2, wherein the dimethyloctadecyl[3-(trimethoxysilyl)propyl] ammonium chloride is present at from about 0.75 wt. % to about 3 wt. %, based on the total weight of the liquid composition.

23. The wet wipe of claim 4, wherein the at least one non-silane quaternary disinfectant comprises from about 0.3 wt. % to about 0.5 wt. % of a mixture of didecyldimethyl ammonium chloride, n-alkyl (50% C14, 40% C12, 10% C16) dimethyl benzyl ammonium chloride, n-alkyl (60% C14, 30% C16, 5% C12, 5% C18) dimethyl benzyl ammonium chloride and n-alkyl (68% C12, 32% C14) dimethyl ethylbenzyl ammonium chloride, based on the total weight of the liquid composition.

24. The wet wipe of claim 5, wherein the isopropanol is present at from about 40 wt. % to about 80 wt. %, based on the total weight of the liquid composition.

* * * * *